(12) United States Patent
Tanzi et al.

(10) Patent No.: US 7,326,540 B2
(45) Date of Patent: Feb. 5, 2008

(54) METHODS FOR IDENTIFYING COMPOUNDS THAT MODULATE STABILIZATION OF SECRETASE-ASSOCIATED PROTEINS

(75) Inventors: Rudolph E. Tanzi, Hull, MA (US); Giuseppina Tesco, Cambridge, MA (US); Young Ho Koh, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 104 days.

(21) Appl. No.: 10/801,087

(22) Filed: Mar. 15, 2004

(65) Prior Publication Data

US 2004/0219610 A1    Nov. 4, 2004

Related U.S. Application Data

(60) Provisional application No. 60/454,828, filed on Mar. 14, 2003, provisional application No. 60/479,165, filed on Jun. 17, 2003.

(51) Int. Cl.
*G01N 33/53* (2006.01)
*G01N 33/567* (2006.01)

(52) U.S. Cl. ..................................................... 435/7.8

(58) Field of Classification Search ..................... None
See application file for complete search history.

(56) References Cited

OTHER PUBLICATIONS

Dewachter I and Van Leuven F. Secretases as targets for the treatment of Alzheimer's disease: the prospects. Lancet, Nov. 2002; 1: 409-416.*
Wilson CA et al. Distinct presenilin-dependent and presenilin-independent gamma-secretases are responsible for total cellular Abeta production. J. Neurosci Res. 2003; 74: 361-369.*
Xia W. Relationship between presenilinase and gamma-secretase. Drug News Perspect. 2003; 16(2): 69-74.*
Aguzzi, A. et al., "Games Played by Rogue Proteins in Prion Disorders and Alzheimer's Disease," *Science* 2003; 302:814-818.
Boucher, P. et al., "LRP: Role in Vascular Wall Integrity and Protection from Atherosclerosis," *Science* 2003; 300:329-332.
Cai, H. et al., "BACE1 is the major β-secretase for generation of Aβ peptides by neurons," *Nature Neuroscience* Mar. 2001; 4(3):233-234.
De Strooper, B. et al., "A presenilin-1-dependent γ-secretase-like protease mediates release of Notch intracellular domain," *Nature* 1999; 398:518-522.
De Stropper, B. et al., "Aph-1, Pen-2, and Nicastrin with Presenelin Generate an Active γ-Secretase Complex," *Neuron* 2003; 38:9-12.
Edbauer, D. et al., "Presenilin and nicastrin regulate each other and determine amyloid beta-peptide production via complex formulation," *PNAS* 2002; 99(13):8666-8671.
Gervais, F.G. et al., "Involvement of Caspases in Proteolytic Cleavage of Alzheimer's Amyloid-β Precursor Protein and Amyloidogenic Aβ Peptide Formation," *Cell* 1999; 97:395-406.
Grüninger-Leitch et al., "Substrate and Inhibitor Profile of BACE (β-Secretase) and Comparison with Other Mammalian Aspartic Proteases," *The Journal of Biological Chemistry* 2002; 277(7):4687-4693.
Haass, C. et al., "Take five-BACE and the γ-secretase quartet conduct Alzheimer's amyloid β-peptide generation," *The EMBO Journal* 2004; 23(3):483-488.
Herreman, A. et al., "γ-Secretase activity requires the presenilin-dependent trafficking of nicastrin through the Golgi apparatus but not its complex glycosylation," *Journal of Cell Science* 2003; 116(6):1127-1136.
Ikeuchi, T. et al., "The Notch Ligands, Deltal and Jagged2, Are Substrates for Presenilin-dependent 'γ-Secretase' Cleavage," *The Journal of Biological Chemistry* 2003; 278(10):7751-7754.
Kang, D.E. et al., "Presenilin Couples the Paired Phosphorylation of β-Catenin Independent of Axin: Implications for β-Catenin Activation in Tumorigenesis," *Cell* 2002; 110:751-762.
Kim, T. et al., "Alternative Cleavage of Alzheimer-Associated Presenilins During Apoptosis by a Caspase-3 Family Protease," *Science* 1997; 277:373-376.
Kitazume, S. et al., "Alzheimer's beta -secretase, beta -site amyloid precursor protein-cleaving enzyme, is responsible for cleavage secretion of Golgi-resident sialyltransferase," *PNAS* 2001; 98(24):13554-13559.
Marambaud, P. et al., "A presenilin-1/γ-secretase cleavage releases the E-cadherin intracellular domain and regulates disassembly of adherens junctions," *The EMBO Journal* 2002; 21(8):1948-1956.
Murphy, M.P. et al., "Overexpression of nicastrin increases Aβ production," *The FASEB Journal* 2003; 17:1138-40.
Puglielli, L. et al., "Ceramide Stabilizes β-Site Amyloid Precursor Protein-cleaving Enzyme 1 and Promotes Amyloid β-Peptide Biogenesis," *The Journal of Biological Chemistry* 2003; 278(22):19777-19783.
Sato, N. et al., "Upregulation of BiP and CHOP by the unfolded-protein response is independent of presenilin expression," *Nature Cell Biology* 2002; 2:863-870.
Selkoe, D. et al., "Notch and Presenilin: Regulated Intramembrane Proteolysis Links Development and Degeneration," *Annu. Rev. Neurosci.* 2003; 26:565-97.
Steinhusen, U. et al., "Cleavage and Shedding of E-cadherin after Induction of Apoptosis," *The Journal of Biological Chemistry* 2001; 276(7):4972-4980.
Struhl, G. et al., "Presenilin is required for activity and nuclear access of Notch in Drosophila," *Nature* 1999; 398:522-525.
Tesco, G. et al., "Caspase Activation Increases β-Amyloid Generation Independently of Caspase Cleavage of the β-Amyloid Precursor Protein (APP)," *The Journal of Biological Chemistry* 2003; 278(46):46074-46080.
Vassar, R. et al., "β-Secretase Cleavage of Alzheimer's Amyloid Precursor Protein by the Transmembrane Aspartic Protease BACE," *Science* 1999; 286:735-741.
Wolfe, M.S. et al., "Two transmembrane aspartates in presenilin-1 required for presenilin endoproteolysis and γ-secretase activity," *Nature* 1999; 398:513-517.
Yuan, J. et al., "Apoptosis in the nervous system," *Nature* 2000; 407: 802-809.

* cited by examiner

Primary Examiner—Elizabeth C. Kemmerer
Assistant Examiner—Kimberly A. Ballard
(74) *Attorney, Agent, or Firm*—Wolf, Greenfield & Sacks, P.C.

(57) ABSTRACT

The invention relates to methods and products for inhibiting caspase activation-induced Aβ accumulation. The invention is useful for diagnosing, preventing, and treating Aβ-accumulation-associated disorders, such as Alzheimer's disease.

7 Claims, 18 Drawing Sheets

METHODS FOR IDENTIFYING COMPOUNDS THAT MODULATE STABILIZATION OF SECRETASE-ASSOCIATED PROTEINS

RELATED APPLICATIONS

This application claims the benefit under 35 U.S.C. § 119(e) of U.S. provisional application Ser. No. 60/454,828, filed Mar. 14, 2003 and of U.S. provisional application Ser. No. 60/479,165, filed Jun. 17, 2003, the disclosures of which are incorporated by reference herein.

GOVERNMENT SUPPORT

This invention was made in part with government support under grant numbers 5P01AG15379 and RO1AG/NS14713 from the National Institutes of Health (NIH). The government may have certain rights in this invention.

FIELD OF THE INVENTION

The invention relates to methods and products for inhibiting caspase activation-induced $A\beta$ accumulation. The invention is useful for diagnosing, preventing, and treating Alzheimer's disease and other disorders associated with $\beta$-secretase and/or $\gamma$-secretase processing of substrates.

BACKGROUND OF THE INVENTION

Alzheimer's disease (AD) is a disorder that causes the gradual loss of brain cells. AD is named after Dr. Alois Alzheimer, who in 1906 noticed changes in the brain tissue of a woman who had died of an unusual mental illness. Upon examination, Dr. Alzheimer found abnormal clumps and tangled bundles of fibers, which are now known as amyloid plaques and neurofibrillary tangles, respectively. Today, these plaques and tangles in the brain are considered hallmarks of AD.

AD results in damage in brain regions associated with thought, memory, and language. Symptoms of AD are progressive and include dementia, which includes characteristics such as loss of memory, problems with reasoning or judgment, disorientation, difficulty in learning, loss of language skills, and decline in the ability to perform routine tasks. Additional AD symptoms may include personality changes, agitation, anxiety, delusions, and hallucinations.

The risk of AD in the population increases with age. It is believed that up to 4 million Americans have AD. The onset of AD is generally after age 60, but in rare instances younger individuals may be afflicted. It is generally believed that approximately 3 percent of men and women ages 65 to 74, and almost half of those age 85 and older have AD.

There is as yet no clear understanding of the cause of AD. Age is a known risk factor and there is some association between family history and early-onset AD. Although a pattern of decline in AD patients is generally clinically recognizable as the disease progresses, reliable diagnostic methods are lacking. The only definitive diagnostic test for AD at this time is to determine whether amyloid plaques and tangles are present in a subject's brain tissue, a determination that can only be done after death. Thus, due to the lack of suitable diagnostic methods, health-care professionals are only able to provide a tentative diagnosis of AD in an individual, particularly at the early to mid stages of the disease. Although these diagnoses can indicate that a person "likely" has AD, the absence of a definitive diagnosis reflects a critical need for more accurate and reliable AD diagnostic tests.

In addition to the absence of reliable diagnostic methods, the are also very limited treatment options available for patients suspected of having and/or diagnosed as having AD. Several drugs have been approved in the US for treatment of early and mid-stage AD, but they have significant detrimental side effects and limited efficacy. The lack of effective treatments for AD means that even with a diagnosis of probable AD, the therapeutic options are quite limited. Thus, there is a significant need for effective compounds and methods for preventing and/or treating AD.

SUMMARY OF THE INVENTION

We have elucidated the roles of secretase pathway associated proteins that are involved in $A\beta$-accumulation-associated disorders, and have developed methods to diagnose $A\beta$-accumulation-associated disorders, e.g. Alzheimer's disease. The invention includes diagnostic methods and methods to identify compounds that modulate the stability of a secretase pathway associated protein, or secretase pathway associated protein complex in a cell, tissue, or subject. The methods and compounds of the invention are also useful for preventing and/or treating $A\beta$-accumulation-associated disorders.

According to one aspect of the invention, methods for diagnosing a disorder associated with altered $\alpha$-secretase and/or $\gamma$-secretase processing of substrates are provided. The methods include measuring the stability of a secretase pathway associated protein in a biological sample from a subject, wherein increased protein stability relative to that in a control biological sample is an indication that the subject has a disorder associated with altered $\beta$-secretase and/or $\gamma$-secretase processing of substrates.

In some embodiments, the disorder associated with altered $\beta$-secretase and/or $\gamma$-secretase processing of substrates is an $A\beta$-accumulation-associated disorder, or is selected from the group consisting of cancer, neurological diseases, immunologic diseases and glycoconjugate metabolism disorders. In preferred embodiments, the $A\beta$-accumulation-associated disorder is selected from the group consisting of Alzheimer's disease, Down's syndrome, cerebrovascular amyloidosis, inclusion body myositis and hereditary inclusion body myopathies, diseases associated with abnormal BACE and/or $\gamma$-secretase activity, ischemia, oxidative stress, head trauma, stroke, hypoglycemia, and any neurodegenerative disorder with increased caspase activation. In certain embodiments, the secretase pathway associated protein is selected from the group consisting of: presenilins (including presenilin 1 and presenilin 2), nicastrin/Aph2, Aph1a, Pen2 and BACE protein. In some embodiments, the subject is human. In some embodiments, the subject is at risk of developing Alzheimer's disease. In some embodiments, the biological sample is selected from the group consisting of cells and tissues. In certain embodiments, the cells are neuronal cells. In certain embodiments, the tissue includes neuronal cells.

According to yet another aspect of the invention, methods for determining onset, progression, or regression, of a disorder associated with altered $\beta$-secretase and/or $\gamma$-secretase processing of substrates in a subject. The methods include measuring the stability of a secretase pathway associated protein in a first biological sample of a subject, measuring the stability of the secretase pathway associated protein in a second biological sample of a subject obtained at a second time, comparing the measurement of stability in the first sample to the measurement of stability in the second sample as a determination of the onset, progression, or regression of the disorder associated with altered β-secretase and/or γ-secretase processing of substrates.

In some embodiments, the disorder associated with altered β-secretase and/or γ-secretase processing of substrates is an Aβ-accumulation-associated disorder, or is selected from the group consisting of cancer, neurological diseases, immunologic diseases and glycoconjugate metabolism disorders. In preferred embodiments, the Aβ-accumulation-associated disorder is selected from the group consisting of Alzheimer's disease, Down's syndrome, cerebrovascular amyloidosis, inclusion body myositis and hereditary inclusion body myopathies, diseases associated with abnormal BACE and/or γ-secretase activity, ischemia, oxidative stress, head trauma, stroke, hypoglycemia, and any neurodegenerative disorder with increased caspase activation. In certain embodiments, the secretase pathway associated protein is selected from the group consisting of: presenilin 1, nicastrin, BACE, Aph1, and Pen2 protein. In some embodiments, the subject is human. In some embodiments, the subject has been diagnosed with Alzheimer's disease or is at risk of developing Alzheimer's disease. In certain embodiments, the biological sample is selected from the group consisting of cells and tissues. In some embodiments, the cells are neuronal cells. In some embodiments, the tissue includes neuronal cells.

According to another aspect of the invention, methods for identifying compounds that modulate caspase activation-induced stabilization of a secretase pathway associated protein are provided. The methods include contacting cells that have been induced to undergo caspase activation with a candidate modulator of secretase pathway associated protein stabilization, and measuring the stability of the secretase pathway associated protein, wherein a difference in the stability of the protein relative to the stability of the protein in untreated cells is an indication that the candidate modulator is a compound that modulates the caspase activation-induced stability of the secretase pathway associated protein. In some embodiments an increase in the stability of the protein relative to the stability of the protein in untreated cells indicates the candidate modulator is an inhibitor of stability of the secretase pathway associated protein. In some embodiments a decrease of the protein relative to the stability of the protein in untreated cells indicates the candidate modulator is an enhancer of stability of the secretase pathway associated protein. In certain embodiments the secretase pathway associated protein is selected from the group consisting of: presenilins (including presenilin 1 and presenilin 2), nicastrin/Aph2, Aph1a, Pen2 and BACE protein. In some embodiments the cells are neuronal cells. In some embodiments the cells are contacted with the candidate modulator before caspase activation induction. In other embodiments the cells are contacted with the candidate modulator after caspase activation induction. In still other embodiments, caspase activation induces apoptosis.

According to another aspect of the invention, methods for treating or preventing a disorder associated with altered β-secretase and/or γ-secretase processing of substrates are provided. The methods include administering to a subject in need of such treatment an effective amount of a compound that is an inhibitor of the caspase activation-associated stabilization or apoptosis-associated stabilization of a secretase pathway associated protein or secretase pathway associated protein complex.

In some embodiments, the disorder associated with altered β-secretase and/or γ-secretase processing of substrates is an Aβ-accumulation-associated disorder, or is selected from the group consisting of cancer, neurological diseases, immunologic diseases and glycoconjugate metabolism disorders. In preferred embodiments, the Aβ-accumulation-associated disorder is selected from the group consisting of Alzheimer's disease, Down's syndrome, cerebrovascular amyloidosis, inclusion body myositis and hereditary inclusion body myopathies, diseases associated with abnormal BACE and/or γ-secretase activity, ischemia, oxidative stress, head trauma, stroke, hypoglycemia, and any neurodegenerative disorder with increased caspase activation. In certain embodiments the secretase pathway associated protein is selected from the group consisting of: presenilins (including presenilin 1 and presenilin 2), nicastrin/Aph2, Aph1a, Pen2 and BACE protein. In some embodiments the subject is a human. In some embodiments the subject has been diagnosed with Alzheimer's disease or is at risk of developing Alzheimer's disease. In some embodiments the compound is linked to a targeting molecule. In some embodiments the targeting molecule's target is a neuronal cell. In certain embodiments the compound is selected from the group consisting of small molecules, polypeptides, and nucleic acids. In some embodiments the polypeptide is an antibody or antigen-binding fragment thereof. In some embodiments the nucleic acid molecule is selected from the group consisting of: antisense molecules, RNAi molecules, and siRNA molecules. In certain embodiments the mode of administration is selected from the group consisting of: implantation, mucosal administration, injection, inhalation, and oral administration. In some embodiments the compound is administered in combination with an additional drug or therapy for treating an Aβ-accumulation-associated disorder.

In another aspect of the invention, methods for preparing a drug formulation are provided. The methods include identifying a compound that inhibits caspase activation-associated stabilization or apoptosis-associated stabilization of a secretase pathway associated protein or secretase pathway associated protein complex by the foregoing methods and formulating the compound for administration to a subject in need of such treatment.

In some embodiments, the drug formulation is used in the treatment of an Aβ-accumulation-associated disorder. Preferred Aβ-accumulation-associated disorders include Alzheimer's disease, Down's syndrome, cerebrovascular amyloidosis, inclusion body myositis and hereditary inclusion body myopathies, diseases associated with abnormal BACE and/or γ-secretase activity, ischemia, oxidative stress, head trauma, stroke, hypoglycemia, and any neurodegenerative disorder with increased caspase activation.

In other embodiments, the drug formulation is used in the treatment of a disease or disorder associated with altered Aβ-secretase and/or γ-secretase processing of substrates. Preferred diseases or disorders include cancer, disorders of cell adhesion, neurological diseases, immunologic diseases, glycoconjugate metabolism disorders and cardiovascular diseases.

Use of the compositions described herein in the preparation of a medicament also is provided. Preferred medicaments include those which are useful in modulation of Aβ accumulation in a subject, particularly for treatment of Aβ accumulation-associated disorders such as Alzheimer's disease, Down's syndrome, cerebrovascular amyloidosis, inclusion body myositis and hereditary inclusion body myopathies, diseases associated with abnormal BACE and/or γ-secretase activity, ischemia, oxidative stress, head trauma, stroke, hypoglycemia, and any neurodegenerative disorder with increased caspase activation.

These and other objects of the invention will be described in further detail in connection with the detailed description of the invention.

BRIEF DESCRIPTION OF THE DRAWINGS

FIG. 2A shows the results of CHO cells overexpressing APP 751 and PS1 were treated with 1 μM staurosporine (STS) or with STS+zVAD (200 μM) for 6 hrs. Secreted $A\beta_{total}$ and $A\beta_{42}$ were measured by ELISA. Both $A\beta_{total}$ and $A\beta_{42}$ were significantly (*=p<0.05) increased in the conditioned media of STS treated cells. zVAD treatment attenuated the apoptosis-induced increases of both $A\beta_{total}$ and $A\beta_{42}$. Each bar represents the mean of triplicate determinations. FIG. 2B shows the $A\beta_{total}$ and $A\beta_{42}$ increase during etoposide-induced apoptosis. CHO cells overexpressing APP 751 and PS1 were treated with 100 μg/mL etoposide, or etoposide+ 200 μM zVAD, for 12 hrs. Secreted $\beta_{total}$ and $A\beta_{42}$ were measured by ELISA. Both $A\beta_{total}$ and $A\beta_{42}$ were significantly (*=p<0.05) increased in the conditioned media of etoposide treated cells compared to control. Treatment with zVAD was able to significantly attenuate apoptosis-induced increases of both $A\beta_{total}$ and $A\beta_{42}$ compared to etoposide treated cells. Each bar represents the mean of triplicate determinations.

FIG. 3A illustrates that BACE protein levels were increased after 24 hrs of STS treatment in CHO cells overexpressing APP751 and PS1WT. Upregulation of BACE occurs also in H4 human neuroglioma (FIG. 3B) and in BACE+/+ mouse fibroblasts (FIG. 3C). BACE−/− mouse fibroblasts were used to show the specificity of the antibody used to detect BACE (anti BACE C-terminus antibody, ABR) (FIG. 3C). Inhibition of caspase activity by zVAD (100 μM) prevented BACE upregulation in all cell types. Instead protein levels of Cu, Zn-SOD did not change, as shown by Western Blot analysis with an anti-Cu, Zn-SOD, indicating the equal protein loading and the specificity of the effect of caspase activation on BACE.

FIG. 6 provides digitized images of Northern blots indicating that caspase activation stabilizes BACE, PS1, nicastrin and Pen2.

FIG. 9a: Apoptosis was induced in CHO cells expressing APP751 and BACE (CAB) by staurosporine (STS) treatment for the time indicated. Western Blot analysis of equivalent amounts of protein (100 µg) from each sample with the antibody, WO2, which specifically recognize amino-acids 1-17 of Aβ region, revealed a fragment of ~90 kDa (APP-Ncasp) generated by caspase cleavage at APP N-terminus, and increased levels of C99 in apoptotic cells. Western blot analysis with anti-BACE antibody revealed an increase in BACE proteins levels. As a loading control, a non-specific band was used. Densitometry analysis was performed using NIH image software. Each bar represents the mean and SEM of at least four experiments. FIG. 9b: Apoptosis was induced in human H4 neuroglioma cells expressing APP751 by STS treatment. Western blot analysis performed with WO2 revealed C99 and C99ΔC31 during time-course experiments. Western blot analysis with anti-caspase 3 active fragment antibody showed caspase 3 activation as early as 6 hours during STS treatment and also limited caspase activity in the 12 (the band is horizontally compressed) and 24 hour control sample (see text for details). Western blot analysis with anti-BACE antibody revealed increased BACE. Cu, Zn-SOD was used as a loading control. Densitometry analysis was performed using NIH image software. Each bar represents the mean and SEM of at least three experiments.

FIG. 10a: Schematic representation of caspase- and secretase-mediated proteolysis of APP and the epitopes recognized by the antibodies, WO2 (line) and ASP-1. The ASP-1 antibody (Oncogene) recognizes only the first aspartyl residue of Aβ region, but does not recognize full-length APP. β, location of cleavage site for Aβ-secretase; γ, location of cleavage site for γ-secretase; casp, location of cleavage site for caspase. DNVD, DYAD, VEVD, and VKMDA are SEQ ID NOs:2-5, respectively. FIG. 10b: Apoptosis was induced in CHO cells expressing APP751 and BACE (CAB) by staurosporine (STS) treatment for the time indicated. Western Blot analysis of equivalent amounts of protein (100 µg) from each sample with WO2 revealed a fragment of ~90 kDa (APP-Ncasp) generated by caspase cleavage at APP N-terminus, and increased levels of C99 in apoptotic cells. FIG. 10c: Western blot analysis with ASP-1 revealed increased levels of C99 in STS-treated cells. Note that ASP-1 did not detect full-length APP (APP-FL). A non-specific band is indicated by *. FIG. 10c: STS treatment led to increased production of C99 as detected by both WO2 and ASP-1, in H4-APP751, as well as SH-SY5Y and N2a neuroblastoma cells expressing only endogenous APP. FIG. 10d: Mass spectrometric analysis of Aβ peptides. CHO-APP751/PS1 cells were treated with STS or STS+zVAD for 6 hours. Conditioned media were collected and IP was performed with 4G8 antibody. 4G8, raised against C-terminus of Aβ, was purchased from Signet (Dedham, Mass.). Immunoprecipitates were analysed using a matrix-assisted laser desorption/ionization time-of-flight mass spectrometer (Applied Biosystems), as described (Wang, R., Sweeney, D., Gandy, S. E. & Sisodia, S. S., *J Biol Chem* 271, 31894-902 (1996)). Spectra were calibrated using internal standard, bovine insulin. Peaks in the spectra are labeled with the corresponding Aβ peptide sequence numbers from the first N-terminal residue. The prefix "m" indicates peaks corresponding to mouse Aβ peptides and the label "insulin, 2+" indicates peaks corresponding to the internal standard used for mass spectra calibration. No Aβ peptides staring at +2 were detected.

FIG. 11a: Apoptosis was induced in CAB, CHO-CC99/PS1 and CHO-APP 751/PS1 by STS treatment for 6 hours with or without zVAD (100 µM). Secreted $A\beta_{1-total}$ was measured by ELISA. $A\beta_{1-total}$ was significantly (*=p<0.05, paired t-test) increased in the conditioned media of apoptotic CAB, CHO—C99/PS1and CHO-APP 751/PS1 cells. Each bar represents the mean and SD of quadruplicate determinations. FIG. 11b: Western blot analysis with the antibody, A8717, detected endogenous APP-FL and overexpressed C99 in CHO-CC99/PS1cells, while overexpressed APP-FL and C83 were detected in CHO-APP751/PS1 cells. FIG. 11c: A431 human epithelial cells were pre-incubated for 30 min in the absence (−) or presence (+) of zVAD-FMK (100 µM), L-685,458 (0.5 µM) or GM6001 (2.5 µM). Cells were then treated with STS for 6 hours to induce apoptosis, and cell extracts were probed with anti-E-cadherin C36 antibody. FIG. 11d: Protein levels of γ-secretase complex components were monitored by Western blotting employing the anti-nicastrin, Ab14, PNT2, H2D2 antibodies. Densitometry analysis was performed using NIH image software. Each bar represents the mean and SEM of at least three experiments. FIG. 11e: Nicastrin was transiently transfected in the A431 cells. Western blot analysis for E-cadherin and γ-secretase complex component was performed as in FIG. 11c and FIG. 11d β-tubulin was used as loading control.

FIG. 13a: Apoptosis was induced in CAB cells by etoposide (ETO) treatment for the time indicated. Western Blot analysis of equivalent amounts of protein (100 µg) from each sample with WO2 detected APP-Ncasp, increased levels of C99, and C99ΔC31 in apoptotic cells. Western blot analysis with anti-BACE, anti-nicastrin, Ab14, PNT2, and H2D2 antibodies revealed an increase in BACE, nicastrin, PS1-NTF, and Pen-2 proteins levels, while Aph1a protein levels were unchanged. A non-specific band was used as a loading control. Densitometry analysis was performed using NIH image software. FIG. 13b: Apoptosis was induced in human H4 neuroglioma cells expressing APP751 by ETO treatment. Western blot analysis with anti-BACE, anti-nicastrin, Ab14, PNT2, and H2D2 antibodies revealed an increase in BACE, nicastrin, PS1-NTF, Pen-2 and Aph1a proteins levels. β-tubulin was used as a loading control. Densitometry analysis was performed using NIH image software.

FIG. 15a: Cycloheximide degradation time-course: BACE, PS1, nicastrin, Pen-2, Aph1a, TACE, and APP proteins were detected by Western blot at various times after addition of CHX (40 µg/ml) only or STS+CHX in H4-APP751 cells. The degradation of BACE and γ-secretase complex proteins was decreased while the degradation of TACE and APP was unchanged during the apoptosis. FIG. 15b: Pulse-chase analysis. H4-APP751 cells were transiently transfected with BACE-Myc cDNA and after 24 hours were metabolically labeled. Lysates from each time point were immunoprecipitated with anti-Myc antibody. For the nicastrin pulse-chase experiments, H4-APP751 cells were used. For PS1 pulse-chase analysis the H4-PS1 cells were metabolically labeled. Lysates from each time point were immunoprecipitated with Ab14 antibody. For the TACE pulse-chase, H4-APP751 cells were metabolically labeled. Lysates from each time point were immunoprecipitated with anti-TACE antibody. Protein amounts were quantified by phosphorimager and represented in the graph. FIG. 15c: Schematic representation of the molecular events occurring during apoptosis associated with increased activity of β-amyloidogenic secretases.

FIG. 16a: Western blot analysis with αPS2loop and Ab14 antibody identified PS1, 2−/− from PS1,2+/+ ES cells. Note that only immature nicastrin was detected in PS1,2−/− cells and that Pen-2 levels were decreased. FIG. 16b: PS1,2−/− ES cells were treated with STS or STS+zVAD for indicated time cour as described in FIG. 15. α-tubulin was used as loading control. FIG. 16c: BACE−/− mouse fibroblasts were treated with STS or STS+zVAD for indicated time-course and then lysates were analyzed by immunoblotting as previously described. As control for the anti-BACE antibody, lysates from CHO cells expressing BACE were included. Cu, Zn-SOD was used as loading control.

DETAILED DESCRIPTION OF THE INVENTION

Figure 1:
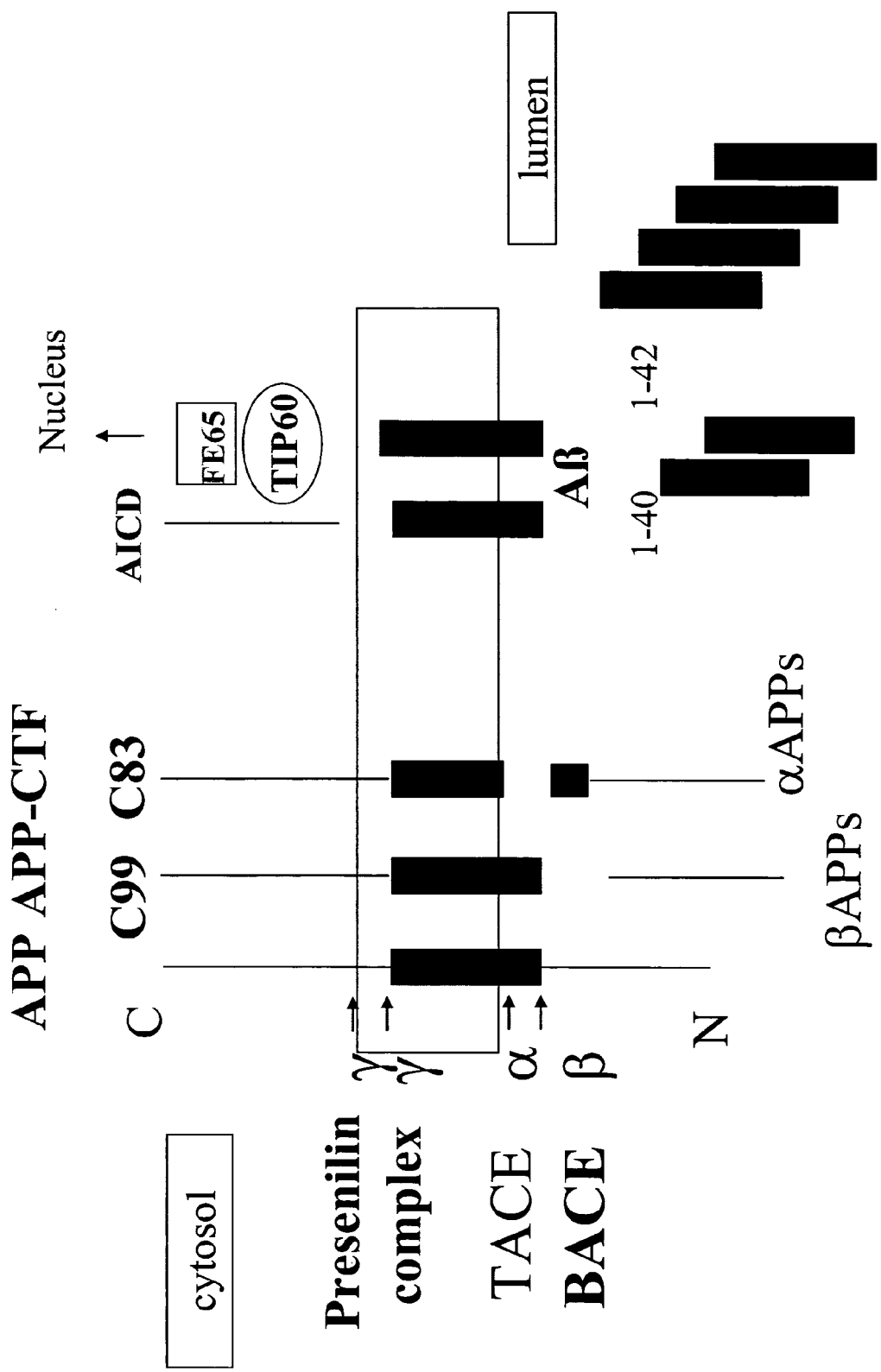
FIG. 1 is a schematic representation of APP secretase-mediated processing.

The physiological processes associated with Alzheimer's disease include the apoptosis-associated accumulation of amyloid plaques and tangles in the neuronal tissues of patients. Part of the AD neuropathological process is the accumulation of the ~4 kDa peptide Aβ in the brain. Aβ is the principle component of senile plaques. The Aβ peptide (37-43 amino acid residues) is derived by serial proteolysis of a larger protein called the amyloid precursor protein (APP) by β-secretase (BACE, beta-site APP-cleaving enzyme) at the N-terminus and by γ-secretase at the C-terminus. APP more commonly undergoes a non-amyloidogenic processing by α-secretases that cleave in the middle of the Aβ-amyloid domain. APP proteolysis by β- and γ-secretases results in the production of β- and α-APP secreted fragments (APPs) as well as C99 and C83 APP-C-terminal fragments (APP-CTFs), respectively. The C99 and C83 APP-CTFs are substrates for γ-secretase resulting in the production of Aβ or p3, respectively. Presenilins are also involved in γ-secretase activity (FIG. 1). β-secretase was identified as a novel membrane-tethered member of the aspartyl proteases, termed BACE (Vassar, R. et al., *Science* 286, 735-41 (1999)). Recent findings have shown that γ-secretase activity requires a set of four proteins including presenilins, nicastrin/Aph2, Aph1a (also known as anterior pharynx defective phenotype 1 protein) and Pen-2 (Haass, C., *Embo J* (2004); De Strooper, B., *Neuron* 38, 9-12 (2003); Aguzzi, A. & Haass, C., *Science* 302, 814-8 (2003)) γ-secretase is an unusual enzyme with the unique ability to cleave its substrates within the transmembrane domain (Selkoe, D. & Kopan, R., *Annu Rev Neurosci* (2003)). In addition to APP and Notch (De Strooper, B. et al., *Nature* 391, 387-90 (1998); De Strooper, B. et al., *Nature* 398, 518-22 (1999); Struhl, G. & Greenwald, I., *Nature* 398, 522-5 (1999)), several additional transmembrane proteins have been identified as γ-secretase substrates (Haass, C., *Embo J* (2004); De Strooper, B., *Neuron* 38, 9-12 (2003)), suggesting a role of presenilins/γ-secretase in receptor-mediated signaling, cell-cell adhesion, synaptic maintenance, and gene transcription.

APP also undergoes "alternative" (caspase-mediated) proteolysis, and it has been proposed that these cleavage events underlie increased Aβ generation associated with apoptosis/caspase activation (Gervais, F. G. et al., *Cell* 97, 395-406 (1999)). As shown herein, however, apoptosis increases Aβ production independently of caspase-mediated cleavage of APP at its C-terminal and N-terminal caspase sites. Here, we also report a novel mechanism of regulation of the β-amyloidogenic secretases that occurs during apoptosis. We show that caspase activation increases the activity of β-amyloidogenic secretases via stabilization of BACE and the γ-secretase complex proteins leading to increased Aβ production.

As used herein, the term "secretase pathway associated protein" means a protein that is involved in the production of Aβ from amyloid precursor protein (APP). The secretase pathway associated proteins of the invention, include, but are not limited to: presenilins (including presenilin 1 and presenilin 2), nicastrin/Aph2, Aph1a, Pen-2, and BACE.

The invention also includes methods and compositions for the diagnosis of AD. Thus, the invention relates in part to the determination and modulation of levels, stabilization, and/or activity of a secretase pathway associated protein, or secretase pathway associated protein complex. As used herein, the term "complex" means an association comprising one or more secretase pathway associated proteins.

The invention includes the recognition that caspase activation induces Aβ accumulation. This recognition permits the modulation of Aβ accumulation for a variety of uses including therapeutic intervention in diseases (e.g., by reducing Aβ accumulation), creation of animal models of disease (e.g., by increasing Aβ accumulation), elucidation of the effects of Aβ accumulation, etc.

Increased Aβ accumulation is the result of increased Aβ production and/or reduced Aβ clearance. Therefore, Aβ accumulation can be modulated (to increase or decrease accumulation depending on the desired result) by modulating Aβ production and/or Aβ clearance to obtain a desired effect. Although not wishing to be bound by any particular theory, it is believed that there are four events that influence Aβ accumulation: Aβ production (e.g., production APP and processing of APP to Aβ), the rate and amount of Aβ aggregation and/or fibril formation, clearance of Aβ aggregates and/or fibrils by cell-mediated events, and direct degradation of Aβ aggregates and/or fibrils by enzymes. Each of these events is a potential target for modulating Aβ accumulation.

In addition to mediating processing of APP, both β-secretase (BACE) and γ-secretase cleave many other substrates, including the sialyltransferase ST6Gal I (Kitazume et al., Proc. Nat'l. Acad. Sci. USA 98(24):13554-13559, 2001); Notch 1, 2, 3 and 4, Delta, Jagged, E-cadherin, Deleted in Colorectal Cancer (DCC), ErbB-4, CD44, low-density lipoprotein receptor-related protein (LRP), and nectin-1-α(DeStrooper, Neuron 38, 9-12, 2003); PSGL-1 (P-selectin glycoprotein ligand-1, cleaved by β-secretase in the juxtamembrane domain), and amyloid precursor-like proteins (APLP 1 and APLP2). For review of gamma-secretase substrates see, e.g., DeStrooper, 2003 and Ikeuchi and Sisodia, J. Biol. Chem. 278(10):7751-7754, 2003; for a review of beta-secretase substrates see e.g., Gruninger-Leitch et al., J. Biol. Chem. 277(7):4687-4693, 2002. Additional gamma-secretase substrates include: CSF1, glutamate receptor subunit 3 (GluR3), p75, Syndecan 3, and N-cadherin.

These additional non-APP substrates of β-secretase and γ-secretase may be involved in cancer (e.g., Notch, Delta, Jagged, cadherin, DCC, ErbB4, p75), disorders of cell adhesion (cadherin), neurological diseases, including Alzheimer's disease (e.g., LRP), immunologic diseases (e.g., CD44, CSF1), glycoconjugate metabolism disorders (ST6Gal I), cardiovascular diseases including atherosclerosis (e.g., LRP; see Boucher et al., Science 300:329-332, 2003) and other diseases (e.g., those involving aberrant leukocyte rolling on the endothelium, transmigration and tissue invasion of leukocytes mediated by PSGL-1). Thus, the stabilization of BACE and gamma-secretase complex components also provides a target for diseases associated with altered beta- and gamma-secretase processing of substrates other than APP.

Abnormal processing of other substrates by β-secretase (BACE) and/or γ-secretase also can be the result of a lack of secretase stabilization. For example, reduced amounts or activities of β-secretase, γ-secretase, or component parts thereof can be responsible for a reduced level of processing of certain substrates, which also can lead to disease states. Moreover, the reduced amounts or activities of β-secretase, γ-secretase, or component parts thereof can affect other biochemical processes, such as intracellular signaling processes. In such conditions, stabilizing or increasing the amounts of the secretases or component parts (e.g., presenilin) can provide beneficial effects in the treatment of diseases in which reduced levels are deleterious. One non-limiting example of this is the effect of a reduced level of presenilin on signaling by β-catenin (see Kang et al., Cell 110:751-762, 2002).

Altered β-secretase and/or γ-secretase processing of substrates therefore can result in a variety of disorders that can be diagnosed and/or treated in accordance with the invention. The term "disorder associated with altered β-secretase and/or γ-secretase processing of substrates" as used herein includes Aβ-accumulation-associated disorders such as Alzheimer's disease as well as other disorders correlated with proteins that also are substrates of β-secretase and/or γ-secretase (cancer, neurological diseases, immunologic diseases, glycoconjugate metabolism disorders, and cardiovascular diseases including atherosclerosis), as described herein.

The methods of the invention in some aspects involve the use of compounds that inhibit caspase activation-induced Aβ production or increase Aβ clearance to reduce Aβ accumulation. Caspase activation in some instances results in apoptosis, and therefore in certain embodiments the methods include the use of compounds that inhibit apoptosis-induced Aβ production to reduce Aβ accumulation. As used herein, the term "Aβ production" means the generation of Aβ, in a cell, tissue, or subject. As used herein, the term "subject" means any mammal that may be in need of treatment with the Aβ production and/or clearance modulating compounds of the invention or may be in need of diagnostic methods of the invention. Subjects include but are not limited to: humans, non-human primates, cats, dogs, sheep, pigs, horses, cows, rodents such as mice, hamsters, and rats.

As used herein, the term "Aβ production-modulating compound" means a compound that modulates the stability of a secretase pathway associated protein or secretase pathway associated protein complex in a cell, tissue, or subject. Compositions of the invention include compounds that modulate caspase activation-induced Aβ production in cells, tissues, and subjects. The methods of the invention involve the administration of compounds that modulate caspase activation-induced Aβ accumulation in neuronal cells and/or tissues and therefore are useful to reduce or prevent Alzheimer's disease, any other diseases or disorders associated with abnormal accumulation of Aβ such as Down's syndrome, cerebrovascular amyloidosis, inclusion body myositis and hereditary inclusion body myopathies and any disease associated with abnormal BACE and/or γ-secretase activity. As used herein, the term "Aβ-accumulation-associated disorder" means Alzheimer's disease, Down's syndrome, cerebrovascular amyloidosis, inclusion body myositis and hereditary inclusion body myopathies, any disease associated with abnormal (increased) BACE activity and any disease associated with abnormal (increased) γ-secretase activity.

The invention includes the recognition that caspase activation can increase Aβ accumulation in neuronal cells and/or tissues (with or without apoptosis) and therefore the invention also provides methods and compositions for diagnosing and treating caspase activation disorders. Therefore, as used herein, Aβ-accumulation-associated disorders include caspase activation disorders. "Caspase activation disorders" include ischemia, oxidative stress, head trauma, stroke, hypoglycemia, and any neurodegenerative disorder with increased caspase activation. A feature of the caspase activation disorders is increased accumulation of Aβ.

The invention involves a variety of assays based upon detecting the level and/or activity of a secretase pathway associated protein and/or secretase pathway associated protein complex, in subjects. The assays include (1) characterizing the impact of levels or activity of a secretase pathway associated protein or secretase pathway associated protein complex in a subject; (2) evaluating a treatment for regulating levels and/or activity of a secretase pathway associated protein or secretase pathway associated protein complex in a subject; (3) selecting a treatment for regulating levels and/or activity of a secretase pathway associated protein or secretase pathway associated protein complex in a subject; and (4) determining regression, progression or onset of a condition characterized by abnormal levels and/or activity of a secretase pathway associated protein or secretase pathway associated protein complex in a subject.

Thus, subjects can be characterized, treatment regimens can be monitored, treatments can be selected and diseases can be better understood using the assays of the present invention. For example, the invention provides in one aspect a method for measuring the level and/or activity of a secretase pathway associated protein or secretase pathway associated protein complex in a subject. As provided by the invention, the level and/or activity of a secretase pathway associated protein or secretase pathway associated protein complex thus correlates with the existence of an $A\beta$ accumulation-associated disorder, e.g. Alzheimer's disease. For example, a level and/or activity that is significantly higher in a subject than a control level may indicated a subject has Alzheimer's disease, whereas a relatively normal level of a secretase pathway associated protein or secretase pathway associated protein complex indicates that the subject does not have an $A\beta$ accumulation-associated disorder of the invention, e.g. Alzheimer's disease.

The assays described herein are carried out on samples obtained from subjects. As used herein, a subject is a human, non-human primate, cow, horse, pig, sheep, goat, dog, cat, or rodent. In all embodiments, human subjects are preferred. The samples used herein are any cell, body tissue, or body fluid sample obtained from a subject. In some embodiments, the cell or tissue sample includes neuronal cells and/or is a neuronal cell or tissue sample.

The biological sample can be located in vivo or in vitro. For example, the biological sample can be a tissue in vivo and the agent specific for a secretase pathway associated protein or secretase pathway associated protein complex can be used to detect the presence of such molecules in the tissue (e.g., for imaging portions of the tissue that include a secretase pathway associated protein or secretase pathway associated protein complex). Alternatively, the biological sample can be located in vitro (e.g., a biopsy such as a tissue biopsy or tissue extract). In a particularly preferred embodiment, the biological sample can be a cell-containing sample. Samples of tissue and/or cells for use in the various methods described herein can be obtained through standard methods. Samples can be surgical samples of any type of tissue or body fluid. Samples can be used directly or processed to facilitate analysis (e.g., paraffin embedding). Exemplary samples include a cell, a cell scraping, a cell extract, a blood sample, a cerebrospinal fluid sample, a tissue biopsy, including punch biopsy, a tumor biopsy, a bodily fluid, a tissue, or a tissue extract or other methods. Samples also can be cultured cells, tissues, or organs.

Particular subjects to which the present invention can be applied are subjects at risk for or known to have an $A\beta$-accumulation-associated disorder. Such disorders may include, but are not limited to: Alzheimer's disease and any other diseases associated with overproduction of $A\beta$ or reduced clearance of $A\beta$ such as Down's syndrome, cerebrovascular amyloidosis, inclusion body myositis and hereditary inclusion body myopathies, any disease associated with abnormal BACE and/or $\gamma$-secretase activity, ischemia, oxidative stress, head trauma, stroke, hypoglycemia, and any neurodegenerative disorder with increased caspase activation.

The assays described herein (see Examples section) include measuring levels and/or activity of a secretase pathway associated protein or secretase pathway associated protein complex. Levels and/or activity of a secretase pathway associated protein or secretase pathway associated protein complex can be measured in a number of ways when carrying out the various methods of the invention. In one type of measurement, the level of a secretase pathway associated protein or secretase pathway associated protein complex is a measurement of absolute levels of a secretase pathway associated protein or secretase pathway associated protein complex. This could be expressed, for example, in terms of molecules per cubic millimeter of tissue. Another measurement of the level of a secretase pathway associated protein or secretase pathway associated protein complex is a measurement of the change in the level and/or activity of the secretase pathway associated protein or secretase pathway associated protein complex over time. This may be expressed in an absolute amount or may be expressed in terms of a percentage increase or decrease over time.

Importantly, levels of a secretase pathway associated protein or secretase pathway associated protein complex are advantageously compared to controls according to the invention. The control may be a predetermined value, which can take a variety of forms. It can be a single value, such as a median or mean. It can be established based upon comparative groups, such as in groups having normal amounts of a secretase pathway associated protein or secretase pathway associated protein complex and groups having abnormal amounts of a secretase pathway associated protein or a secretase pathway associated protein complex. Another example of comparative groups would be groups having a particular disease (e.g., Alzheimer's disease), condition or symptoms, and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or amounts of a secretase pathway associated protein or secretase pathway associated protein complex and the highest quadrant or quintile being individuals with the highest risk or amounts of a secretase pathway associated protein or secretase pathway associated protein complex.

The predetermined value of course, will depend upon the particular population selected. For example, an apparently healthy population will have a different 'normal' range than will a population that is known to have a condition related to $A\beta$ accumulation. Accordingly, the predetermined value selected may take into account the category in which an individual falls. Appropriate ranges and categories can be selected with no more than routine experimentation by those of ordinary skill in the art. By abnormally high it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples.

The various assays used to determine the levels and/or activity of a secretase pathway associated protein or secretase pathway associated protein complex include: assays, such as described in the Examples section herein, and assays such as using materials that specifically bind to a secretase pathway associated protein or secretase pathway associated protein complex (e.g., immunoassays); gel electrophoresis; NMR; and the like. Immunoassays may be used according to the invention including sandwich-type assays, competitive binding assays, one-step direct tests and two-step tests such as routinely practiced by those of ordinary skill in the art.

As mentioned above, it is also possible to characterize the existence of an Aβ accumulation-associated disorder by monitoring changes in the absolute or relative amounts or activity of a secretase pathway associated protein or secretase pathway associated protein complex over time. For example, it is expected that an increase that amount or activity of a secretase pathway associated protein, or secretase pathway associated protein complex correlates with increasing severity of an Aβ accumulation-associated disorder. Accordingly one can monitor levels and/or activity of a secretase pathway associated protein or secretase pathway associated protein complex to determine if the status (e.g. severity, existence) of an Aβ accumulation-associated disorder of a subject is changing. Changes in relative or absolute levels and/or activity of a secretase pathway associated protein or secretase pathway associated protein complex of greater than 0.1% may indicate an abnormality. Preferably, the change in levels and/or activity of a secretase pathway associated protein or secretase pathway associated protein complex, which indicates an abnormality, is greater than 0.2%, greater than 0.5%, greater than 1.0%, 2.0%, 3.0%, 4.0%, 5.0%, 7.0%, 10%,. 15%, 20%, 25%, 30%, 40%, 50%, or more. Other changes, (e.g. increases or reductions) in levels or amounts and/or activity of a secretase pathway associated protein or secretase pathway associated protein complex over time may indicate an onset, progression, regression, or remission of the Aβ accumulation-associated disorder in the subject. As described above, in some disorders a decrease in level and/or activity of a secretase pathway associated protein or secretase pathway associated protein complex may mean regression of the disorder. Such a regression may be associated with a clinical treatment of the disorder thus the methods of the invention can be used to determine the efficacy of a therapy for an Aβ-accumulation-associated disorder (e.g. Alzheimer's disease). In some disorders an increase in level and/or activity of a secretase pathway associated protein or secretase pathway associated protein complex may mean progression or onset of the disorder.

The invention in another aspect provides a diagnostic method to determine the effectiveness of treatments for abnormal levels or activity of a secretase pathway associated protein or secretase pathway associated protein complex. The term "evaluation of treatment" as used herein, means the comparison of a subject's levels and/or activity of a secretase pathway associated protein or secretase pathway associated protein complex measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours after the time of first sample collection.

The comparison of levels and/or activity of a secretase pathway associated protein or secretase pathway associated protein complex in two or more samples, taken on different days, is a measure of level of the subject's diagnostic status for an Aβ accumulation-associated disorder of the invention and allows evaluation of the treatment to regulate levels and or activity of a secretase pathway associated protein or secretase pathway associated protein complex. The comparison of a subject's levels and/or activity of a secretase pathway associated protein or secretase pathway associated protein complex measured in samples obtained on different days provides a measure of the status of the Aβ accumulation-associated disorder to determine the effectiveness of any treatment to regulate levels and/or activity of a secretase pathway associated protein or secretase pathway associated protein complex in the subject.

As will be appreciated by those of ordinary skill in the art, the evaluation of the treatment also may be based upon an evaluation of the symptoms or clinical end-points of the associated disease. In some instances, the subjects to which the methods of the invention are applied are already diagnosed as having a particular condition or disease. In other instances, the measurement will represent the diagnosis of the condition or disease. In some instances, the subjects will already be undergoing drug therapy for an Aβ accumulation-associated disorder (e.g. Alzheimer's disease), while in other instances the subjects will be without present drug therapy for an Aβ accumulation-associated disorder.

Agents, e.g. antibodies and/or antigen-binding fragments thereof, that specifically bind to a secretase pathway associated protein or secretase pathway associated protein complex, are useful in additional diagnostic methods. As described herein, the antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies or antigen-binding fragments thereof may be used for example to identify tissues expressing protein or to purify protein.

As detailed herein, the foregoing antibodies or antigen-binding fragments thereof and other binding molecules may be used for example to identify a secretase pathway associated protein or secretase pathway associated protein complex. Antibodies also may be coupled to specific diagnostic labeling agents for imaging of cells and tissues with abnormal levels and/or activity of a secretase pathway associated protein or secretase pathway associated protein complex; or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art.

Using methods described herein, agents (e.g., antibodies or antigen-binding fragments thereof) can be identified and prepared that bind specifically to a secretase pathway associated protein or to secretase pathway associated protein complexes. As used herein, "binding specifically to" means capable of distinguishing the identified material from other materials sufficient for the purpose to which the invention relates. Thus, "binding specifically to" a secretase pathway associated protein means the ability to bind to and distinguish presenilins (including presenilin 1), nicastrin/Aph2, BACE, Aph1a and/or Pen-2 proteins from other proteins. Binding specifically to a secretase pathway associated protein complex that includes one or more secretase pathway associated proteins means binding to and distinguishing the complex from individual presenilins (including presenilin 1), nicastrin/Aph2, BACE, Aph1, and/or Pen2 proteins, or distinguishing from other complexes of proteins.

The invention also provides agents (e.g. antibodies) for use in methods to stabilize or destabilize a secretase pathway associated protein or secretase pathway associated protein complex. In such methods, the antibodies recognize and bind specifically to a secretase pathway associated protein or secretase pathway associated protein complex. Methods to stabilize or destabilize a secretase pathway associated protein or a secretase pathway associated protein complex, may be used to treat Aβ accumulation-associated disorders of the invention, for example, methods to destabilize the proteins or complexes thereof, may be used to prevent or treat Alzheimer's disease.

Agents that bind to a secretase pathway associated protein and fragments thereof, or bind to a secretase pathway associated protein complex, include polypeptide agents. Such polypeptides include polyclonal and monoclonal antibodies, prepared according to conventional methodology. Antibodies that bind a secretase pathway associated protein, fragment thereof, or a secretase pathway associated protein complex are useful for determining secretase pathway associated proteins, fragments thereof, or secretase pathway associated protein complexes. Such antibodies include, but are not limited to: antibodies that bind specifically to a secretase pathway associated protein, antibodies that bind specifically to fragments of a secretase pathway associated protein, and antibodies that bind specifically to secretase pathway associated protein complexes. Certain antibodies useful in the methods of the invention already are known in the art and include for example, the antibodies provided in the Examples section herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859, 205. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to a secretase pathway associated protein, fragment thereof, or secretase pathway associated protein complex. These polypeptides may be derived also from sources other than antibody technology. For example, such polypeptide-binding agents can be provided by degenerate peptide libraries, which can be readily prepared in solution, in immobilized form or as phage display libraries. Combinatorial libraries also can be synthesized of peptides containing one or more amino acids. Libraries further can be synthesized of peptoids and non-peptide synthetic moieties.

A wide variety of assays to identify pharmacological agents that modulate the stability of a secretase pathway associated protein and/or secretase pathway associated protein complex can be used in accordance with the aspects of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds. In some embodiments, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Cells include cells that transformed to express a secretase pathway associated protein, or fragment or variant thereof, and cells treated using methods described herein to modulate (e.g. inhibit or enhance) the level and/or activity of a secretase pathway associated protein or secretase pathway associated protein complex.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

An assay may be used to identify candidate agents that modulate 1) production of Aβ, and/or 2) stability and/or activity of a secretase pathway associated protein or secretase pathway associated protein complex. In general, the mixture of the foregoing assay materials is incubated under conditions whereby, but for the presence of the candidate pharmacological agent, Aβ production occurs. It will be understood that a candidate pharmacological agent that identified as a modulating agent may be identified as reducing or eliminating Aβ production. A reduction in Aβ production need not be the absence of Aβ production, but may be a lower level of Aβ production. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the stability of a secretase pathway associated protein, secretase pathway associated protein complex, and/or Aβ production is detected by any convenient method available to the user.

Aβ production may be modulated using methods and/or compounds that modulate the stabilization or activity of a secretase pathway associated protein, or secretase pathway associated protein complex. As used herein, the term "modulate" means to change, which in some embodiments means to "enhance" and in other embodiments, means to "inhibit". In some embodiments, stabilization or activity of a secretase pathway associated protein or secretase pathway associated protein complex is reduced or inhibited. It will be understood that reduction may mean reduction to zero or may mean reduction to a level below a normal level, a previous level, or a control level.

The Aβ production modulating molecules of the invention may include small molecules, polypeptides, (for example, competitive ligands and antibodies, or antigen-binding fragments thereof), and nucleic acids. For example, compositions of the invention may include nucleic acids that encode a molecule that stability and/or activity of a secretase pathway associated protein, fragments and/or complexes thereof, nucleic acids that bind to other nucleic acids, [e.g. for antisense, RNAi, or small interfering RNA (siRNA) methods], or may be polypeptides that reduce the stability and/or activity of a secretase pathway associated protein or complex that includes a secretase pathway associated protein. Such polypeptides include, but are not limited to antibodies or antigen-binding fragments thereof.

Various methods may be used to decrease Aβ accumulation. Aβ accumulation may be decreased using methods to decrease the level, stabilization, and/or activity of secretase pathway associated proteins, or a secretase pathway associated protein complex. For example, methods of the invention include 1) the administration of molecules that are antisense of the nucleic acids that encode a secretase pathway associated protein, 2) RNAi and/or siRNA inhibition methods, and/or 3) administration of antibodies that block the functional activity of the proteins in the production of Aβ (e.g. block interaction of the secretase pathway associated proteins). The methods of reducing activity of the proteins may also include administering polypeptides or nucleic acids that encode polypeptides that are variants of the secretase pathway associated proteins and are not fully functional. Such dominant negative variants may compete with the functional endogenous versions in a cell, tissue, or subject, and thereby reduce the Aβ production activity of the endogenous secretase pathway associated proteins or secretase pathway associated protein complexes. The Aβproduction-modulating compounds of the invention, which include for example, antisense oligonucleotides, RNAi and/or siRNA oligonucleotides, antibodies, nucleic acids, an/or polypeptides may be administered as part of a pharmaceutical composition.

In some embodiments of the invention, the level, stability, and/or activity of a secretase pathway associated protein, or secretase pathway associated protein complex may be increased, for example, to produce cell or animal models of Alzheimer's disease or other neurological disorder. In these embodiments, the level of expression or functional activity of one or more secretase pathway associated proteins may be increased using methods such as administration of nucleic acids that encode the molecules, or other methods that enhance expression of the molecules. Methods to increase the stability or activity of a secretase pathway associated protein, or secretase pathway associated protein complex may also include the use of binding agents, e.g. antibodies, to stabilize the proteins or complexes of one or more of the proteins.

One set of embodiments of the aforementioned Aβ production-modulating compositions and methods include the use of antisense molecules or nucleic acid molecules that reduce expression of genes via RNA interference (RNAi or siRNA). One example of the use of antisense, RNAi or siRNA in the methods of the invention, although not intended to be limiting is their use to decrease the level of expression of one or more secretase pathway associated proteins. The antisense oligonucleotides, RNAi, or siRNA nucleic acid molecules used for this purpose may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods, which may be carried out manually or by an automated synthesizer. They also may be produced recombinantly by vectors.

In some embodiments of the invention, the antisense oligonucleotides also may include "modified" oligonucleotides. That is, the oligonucleotides may be modified in a number of ways, which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars that are covalently attached to low molecular weight organic groups other than a hydroxyl group at the 3' position and other than a phosphate group at the 5' position. Thus, modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acid molecules encoding proteins of the invention, together with pharmaceutically acceptable carriers.

The methods to modulate Aβ accumulation also include methods to increase expression of fragments or variants of a secretase pathway associated protein that may have reduced function (e.g., dominant negative molecules). Additionally, the invention includes methods that include cells or models of Alzheimer's disease, thereby including methods that increase the stability, activity, or function of a secretase pathway associated protein. Thus, it will be recognized that the invention embraces the use of sequences that encode a secretase pathway associated protein or fragment or variant thereof, in expression vectors, as well their use to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, including neurons, mast cells, fibroblasts, oocytes, monocytes, lymphocytes, and leukocytes, and they may be primary cells or cell lines. Specific examples include neurons, keratinocytes, peripheral blood leukocytes, bone marrow stem cells and embryonic stem cells. The expression vectors require that the pertinent sequence, i.e., those nucleic acids described supra, be operably linked to a promoter.

The invention also permits the construction of polypeptide gene "knock-outs" or "knock-ins" in cells and in animals, providing materials for studying certain aspects of disorders associated with a secretase pathway associated protein. For example, a knock-in mouse may be constructed and examined for clinical parallels between the model and characteristics and symptoms found in subjects with Alzheimer's disease. Thus, animal or cell models may be constructed in which the level, stability, activity and/or function of a secretase pathway associated protein is increased. Such a cellular or animal model may be useful for assessing treatment strategies for Aβ accumulation-associated disorders, e.g. Alzheimer's disease. This type of "knock-in" model provides a model with which to evaluate the effects of candidate pharmacological agents (e.g. inhibitory effects) on a living animal that has an abnormal level of Aβ production.

According to still a further aspect of the invention, a transgenic non-human animal comprising an expression vector of the invention is provided, including a transgenic non-human animal which has altered expression of molecule that modulates the level of presenilin1 and/or the stability of a secretase pathway associated protein.

As used herein, "transgenic non-human animals" includes non-human animals having one or more exogenous nucleic acid molecules incorporated in germ line cells and/or somatic cells. Thus the transgenic animal include "knockout" animals having a homozygous or heterozygous gene disruption by homologous recombination, animals having episomal or chromosomally incorporated expression vectors, etc. Knock-out animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to nucleic acid molecules of the invention to increase or decrease expression of the encoded polypeptide molecule in a regulated or conditional manner. Trans-acting negative or positive regulators of polypeptide activity or expression also can be operably linked to a conditional promoter as described above. Such trans-acting regulators include antisense nucleic acid molecules, nucleic acid molecules that encode dominant negative molecules, ribozyme molecules specific for nucleic acid molecules, and the like. The transgenic non-human animals are useful in experiments directed toward testing biochemical or physiological effects of diagnostics or therapeutics for conditions characterized by increased or decreased levels of presenilin and/or increased or decreased stability of a secretase pathway associated protein. Other uses will be apparent to one of ordinary skill in the art. Thus, the invention also permits the construction of gene "knock-outs" in cells and in animals, providing materials for studying certain aspects of $A\beta$ accumulation-associated disorders.

According to another aspect of the invention, methods to modulate $A\beta$ accumulation include use of one or more isolated secretase pathway associated proteins or fragments thereof as $A\beta$ accumulation-modulating compounds. Such proteins or fragments thereof may be useful to generate antibodies to single secretase pathway associated proteins or to complexes of one or more secretase pathway associated proteins. Fragments of one or more secretase pathway associated proteins may also be useful to replace fully functional endogenous secretase pathway proteins. If a secretase pathway associated protein, or fragment thereof does not exhibit the secretase pathway associated protein's function, it may be useful to replace or dilute out the filly functional endogenous secretase pathway associated protein in a subject.

Proteins of the invention, and fragments thereof, can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as those presented by MHC molecules on the surface of a cell for immune recognition) also can be synthesized chemically using well-established methods of peptide synthesis.

Thus, as used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure proteins may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, e.g. isolated from other proteins.

The prevention and treatment methods of the invention include administration of $A\beta$ accumulation-modulating compounds. Various techniques may be employed for introducing $A\beta$ accumulation-modulating compounds of the invention to cells, depending on whether the compounds are introduced in vitro or in vivo in a host. In some embodiments, the $A\beta$ accumulation-modulating compounds target neuronal cells and/or tissues. Thus, the $A\beta$ accumulation-modulating compounds can be specifically targeted to neuronal tissue (e.g. neuronal cells) using various delivery methods, including, but not limited to: administration to neuronal tissue, the addition of targeting molecules to direct the compounds of the invention to neuronal cells and/or tissues. Additional methods to specifically target molecules and compositions of the invention to brain tissue and/or neuronal tissues are known to those of ordinary skill in the art.

In some embodiments of the invention, an $A\beta$ accumulation-modulating compound of the invention may be delivered in the form of a delivery complex. The delivery complex may deliver the $A\beta$ accumulation-modulating compound into any cell type, or may be associated with a molecule for targeting a specific cell type. Examples of delivery complexes include an $A\beta$ accumulation-modulating compound of the invention associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some delivery complexes may be sufficiently stable in vivo to prevent significant uncoupling prior to internalization by the target cell. However, the delivery complex can be cleavable under appropriate conditions within the cell so that the $A\beta$ accumulation-modulating compound is released in a functional form.

An example of a targeting method, although not intended to be limiting, is the use of liposomes to deliver an $A\beta$ accumulation-modulating compound of the invention into a cell. Liposomes may be targeted to a particular tissue, such as neuronal cells, by coupling the liposome to a specific ligand such as a monoclonal antibody, sugar, glycolipid, or protein. Such proteins include proteins or fragments thereof specific for a particular cell type, antibodies for proteins that undergo internalization in cycling, proteins that target intracellular localization and enhance intracellular half life, and the like.

Liposomes are commercially available from Gibco BRL, for example, as LIPOFECTIN™ and LIPOFECTAC™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, 3:235-241 (1985).

When administered, the Aβ accumulation-modulating compounds (also referred to herein as therapeutic compounds and/or pharmaceutical compounds) of the present invention are administered in pharmaceutically acceptable preparations. Such preparations may routinely contain pharmaceutically acceptable concentrations of salt, buffering agents, preservatives, compatible carriers, and optionally other therapeutic agents.

The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, intravenous, intraperitoneal, intramuscular, intranasal, intracavity, subcutaneous, intradermal, or transdermal.

The therapeutic compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bio-erodible implants that are useful in accordance with this method are described in PCT International application no. PCT/US/03307 (Publication No. WO 95/24929, entitled "Polymeric Gene Delivery System". PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in PCT/US/03307. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used. The polymeric matrix composition can be selected to have both favorable degradation rates and also to be formed of a material that is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver agents of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention are delivered using the bioerodible implant by way of diffusion, or more preferably, by degradation of the polymeric matrix. Exemplary synthetic polymers that can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Use of a long-term sustained release implant may be particularly suitable for treatment of established neurological disorder conditions as well as subjects at risk of developing a neurological disorder. "Long-term" release, as used herein, means that the implant is constructed and arranged to deliver therapeutic levels of the active ingredient for at least 7 days, and preferably 30-60 days. The implant may be positioned at or near the site of the neurological damage or the area of the brain or nervous system affected by or involved in the neurological disorder. Long-term sustained release implants are well known to those of ordinary skill in the art and include some of the release systems described above.

Some embodiments of the invention include methods for treating a subject to reduce the risk of a disorder associated with abnormal levels and/or activity of a secretase pathway associated protein or secretase pathway associated protein complex. The methods involve selecting and administering to a subject who is known to have, is suspected of having, or is at risk of having an abnormal level and/or activity of a secretase pathway associated protein or secretase pathway associated protein complex, an β accumulation-modulating compound for treating the disorder. Preferably, the an Aβ accumulation-modulating compound is a compound for modulating (e.g. inhibiting) levels and/or activity of a secretase pathway associated protein or secretase pathway associated protein complex and is administered in an amount effective to modulate (reduce) levels and/or activity of a secretase pathway associated protein or secretase pathway associated protein complex.

Another aspect of the invention involves reducing the risk of a disorder associated with abnormal levels and/or activity of a secretase pathway associated protein or secretase pathway associated protein complex means using treatments and/or medications to modulate levels of a secretase pathway associated protein or secretase pathway associated protein complex, therein reducing, for example, the subject's risk of an Aβ accumulation-associated disorder of the invention.

In a subject determined to have an Aβ-accumulation-associated disorder, an effective amount of an Aβ accumulation-modulating compound is that amount effective to modulate (e.g. increase of decrease) levels of Aβ accumulation in the subject. For example, in the case of Alzheimer's disease an effective amount may be an amount that inhibits (reduces) the abnormally high level and/or activity of a secretase pathway associated protein or secretase pathway associated protein complex, in the subject.

A response to a prophylatic and/or treatment method of the invention can, for example, also be measured by determining the physiological effects of the treatment or medication, such as the decrease or lack of disease symptoms following administration of the treatment or pharmacological agent. Other assays will be known to one of ordinary skill in the art and can be employed for measuring the level of the response. For example, the behavioral and neurological diagnostic methods that are used to ascertain the likelihood that a subject has Alzheimer's disease, and to determine the putative stage of the disease can be used to ascertain the level of response to a prophylactic and/or treatment method of the invention. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormal levels and/or activity of a secretase pathway associated protein or secretase pathway associated protein complex.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to modulate Aβ accumulation, and/or the level or activity of a secretase pathway associated protein or secretase pathway associated protein complex and reduce, prevent, or eliminate the Aβ accumulation-associated disorder. For example, testing can be performed to determine the level and/or activity of a secretase pathway associated protein or secretase pathway associated protein complex in a subject's tissue and/or cells. Additional tests useful for monitoring the onset, progression, and/or remission, of Aβ accumulation-associated disorders such as those described above herein, are well known to those of ordinary skill in the art. As would be understood by one of ordinary skill, for some disorders (e.g. Alzheimer's disease) an effective amount would be the amount of a pharmacological agent of the invention that decreases the level and/or activity of a secretase pathway associated protein or secretase pathway associated protein complex to a level and/or activity that diminishes the disorder, as determined by the aforementioned tests.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

The pharmaceutical compositions used in the foregoing methods preferably are sterile and contain an effective amount of a pharmacological agent for producing the desired response in a unit of weight or volume suitable for administration to a patient. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent of the invention may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Various modes of administration will be known to one of ordinary skill in the art which effectively deliver the pharmacological agents of the invention to a desired tissue, cell, or bodily fluid. The administration methods include: topical, intravenous, oral, inhalation, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g, Remington's Pharmaceutical Sciences, 18th edition, 1990) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration (e.g., intra-organ) and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases including Aβ accumulation-associated disorders of the invention. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the pharmacological agents and/or compositions of the invention.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal. The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

In general, the treatment methods involve administering an agent to modulate the level and/or activity of a secretase pathway associated protein or secretase pathway associated protein complex. Thus, these methods include gene therapy applications. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements, which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

In certain embodiments, the method for treating a subject with a disorder characterized by abnormal levels and/or activity of a secretase pathway associated protein or secretase pathway associated protein complex, involves administering to the subject an effective amount of a nucleic acid molecule to treat the disorder. In certain of these embodiments, the method for treatment involves administering to the subject an effective amount of an antisense, RNAi, or siRNA oligonucleotide to reduce the level of a secretase pathway associated protein or secretase pathway associated protein complex and thereby, treat the disorder. An exemplary molecule for modulating the level and/or activity of a secretase pathway associated protein or secretase pathway associated protein complex is an antisense molecule that is selective for the nucleic acid encoding a secretase pathway associated protein. Alternatively, the method for treating a subject with a disorder characterized by abnormal levels and/or activity of a secretase pathway associated protein or secretase pathway associated protein complex involves administering to the subject an effective amount of a secretase pathway associated protein (or the nucleic acid that encodes such a protein) that has reduced or no normal secretase pathway associated protein function to treat the disorder.

In yet another embodiment, the treatment method involves administering to the subject an effective amount of a binding polypeptide (e.g antibody, or antigen-binding fragment thereof) to modulate binding between one or more proteins of the invention and, thereby, treat the disorder. In some embodiments, the treatment method involves administering to the subject an effective amount of a binding polypeptide to inhibit or enhance the level and/or activity of a secretase pathway associated protein or secretase pathway associated protein complex to decrease or increase $A\beta$ production activity, respectively. In certain preferred embodiments, the binding polypeptide is an antibody or an antigen-binding fragment thereof; more preferably, the antibodies or antigen-binding fragments are labeled with one or more cytotoxic agents.

According to yet another aspect of the invention, expression vectors comprising any of the isolated nucleic acid molecules of the invention, preferably operably linked to a promoter are provided. In a related aspect, host cells transformed or transfected with such expression vectors also are provided. Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a protein of the invention, fragment, or variant thereof. The heterologous DNA (RNA) is placed under operable control of transcriptional elements to permit the expression of the heterologous DNA in the host cell.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, a virus vector for delivering a nucleic acid molecule encoding a secretase pathway associated protein of the invention (e.g. presenilin 1, nicastrin, BACE, Aph1and/or Pen2 proteins), fragment thereof, antisense molecule, RNAi, or siRNA molecule of the invention, is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339, 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., *J. Virol.* 70:3781-3787, 1996), Sindbis virus (Pugachev et al., *Virology* 212: 587-594, 1995), and Ty virus-like particle (Allsopp et al., *Eur. J. Immunol* 26:1951-1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N. J. (1991).

Preferably the foregoing nucleic acid delivery vectors: (1) contain exogenous genetic material that can be transcribed and translated in a mammalian cell and that can suppress Aβ accumulation-associated disorders, and preferably (2) contain on a surface a ligand that selectively binds to a receptor on the surface of a target cell, such as a mammalian cell, and thereby gains entry to the target cell.

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

In addition to delivery through the use of vectors, nucleic acids of the invention may be delivered to cells without vectors, e.g. as "naked" nucleic acid delivery using methods known to those of skill in the art.

The invention will be more fully understood by reference to the following examples. These examples, however, are merely intended to illustrate the embodiments of the invention and are not to be construed to limit the scope of the invention.

EXAMPLES

Example 1

Apoptosis Enhances $A\beta_{total}$ and $A\beta_{1-42}$ Production

Figure 2:
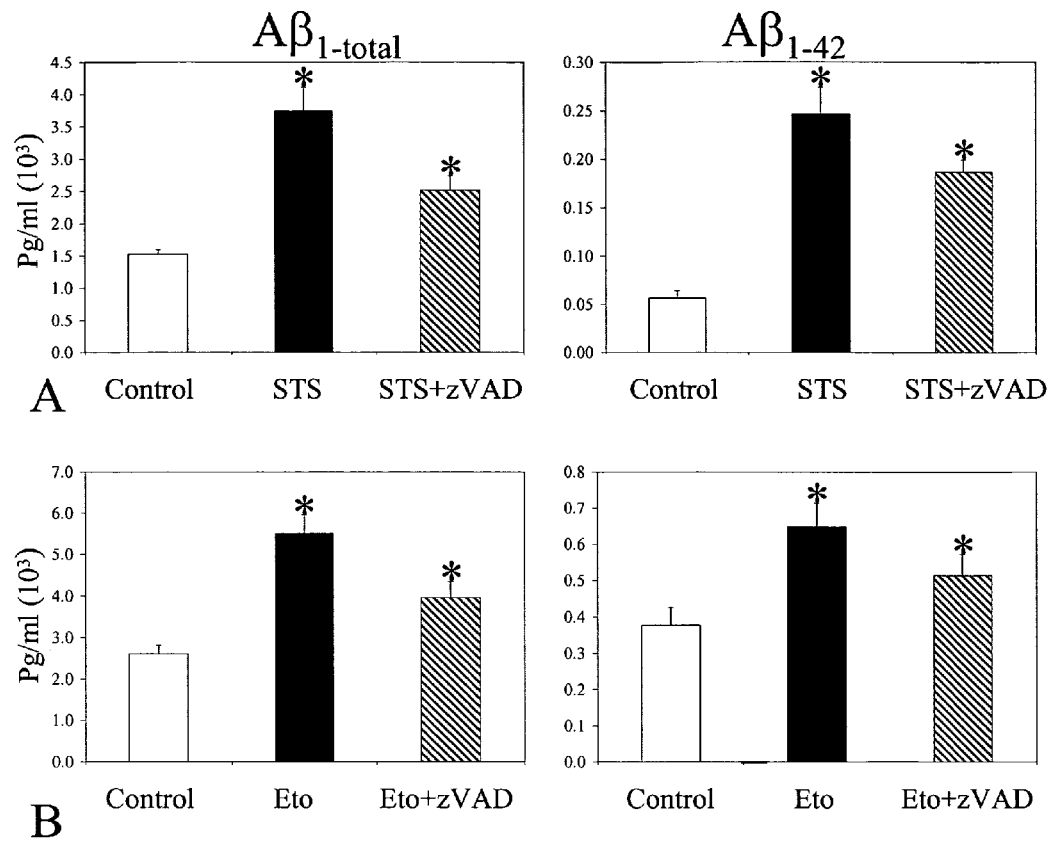
FIG. 2 shows bar graphs of $A\beta_{total}$ and $A\beta_{42}$ increase during staurosporine and etoposide-induced apoptosis.

We examined Aβ generation induced by apoptosis in CHO cell lines. We used CHO cell lines stably overexpressing both APP751 and PS1 WT. For the induction of apoptosis, we used 1 µM staurosporine (STS) in serum free media. Secreted Aβ was measured in the conditioned media of cells treated with STS for 6 hrs using a sensitive ELISA assay [courtesy of Dr. Dennis Selkoe; M. S. Wolfe et al., Nature 398, 513-7 (1999)]. Both $A\beta_{total}$ and $A\beta_{1-42}$ were significantly increased in STS-treated cells (p<0.05 t-test). When cells were pretreated with zVAD (200 µM) for 1 hr before STS, $A\beta_{total}$ and $A\beta_{1-42}$ were significantly reduced compared to STS-treated cells (p<0.05 t-test) (FIG. 2A). STS treatment clearly induced apoptosis after 6 hrs (caspase 3 was activated and cells were TUNEL positive).

Apoptosis was also induced with etoposide, a topoisomerase II inhibitor, to determine whether the effect on Aβ generation was due to apoptosis and independent of the STS drug treatment. In these studies, cells were treated with etoposide (100 µg/mL) for 12 hrs. Treatment with either STS for 6 hrs or etoposide for 12 hrs induced from 10 to 20% of cell death assayed by MTT assay, which is a colorimetric short-term suspension culture assay in which the yellow tetrazolium salt (MTT) is reduced in metabolically active cells to form insoluble purple formazan crystals, which are solubilized by the addition of a detergent. The color was then quantified by spectrophotometric means. Both secreted $A\beta_{total}$ and $A\beta_{1-42}$ were increased (FIG. 2B).

Example 2

Figure 3:
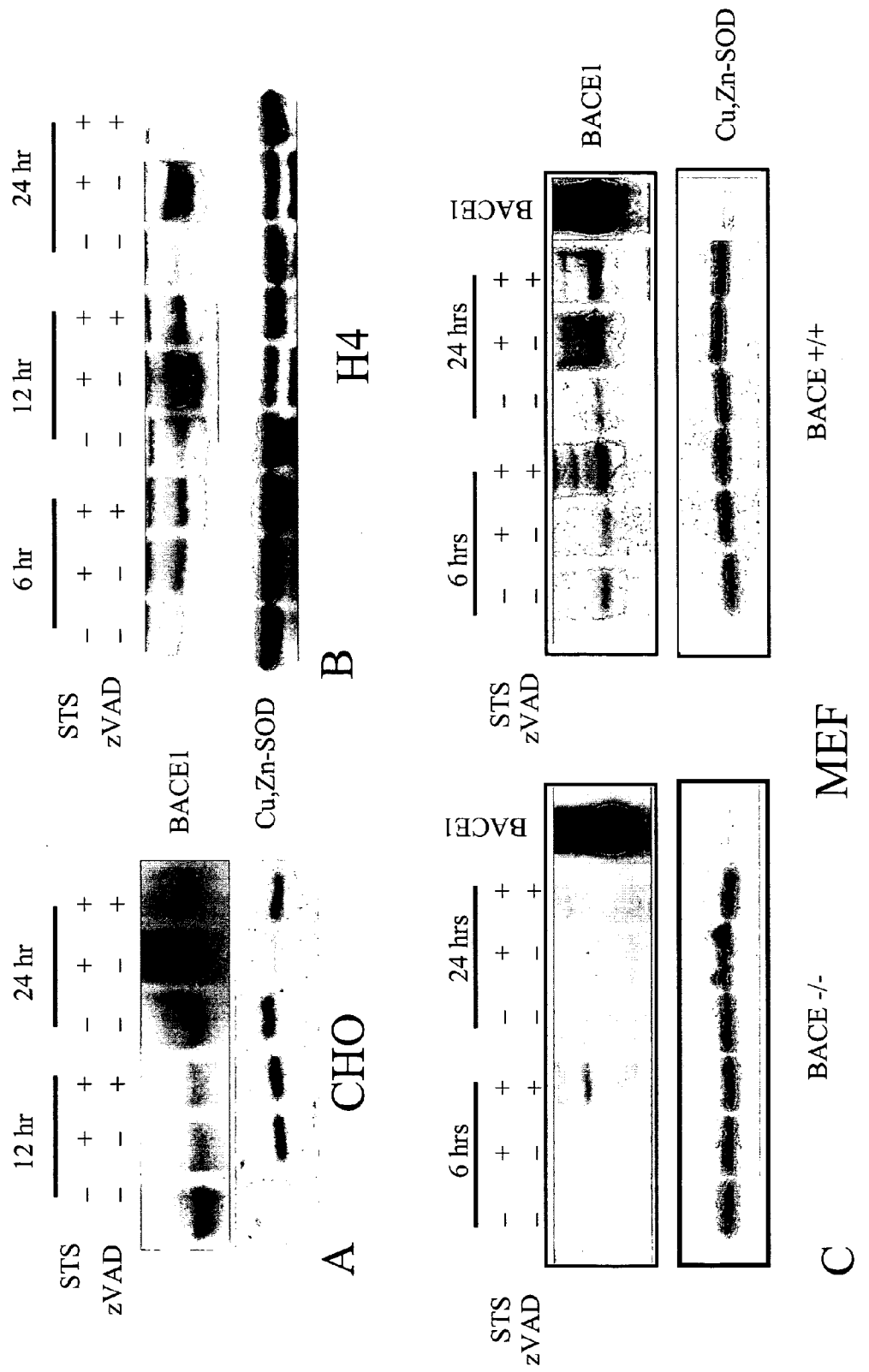
FIG. 3 shows digitized images of Western blots indicating that apoptosis upregulates protein levels of BACE in various cell-types.

Apoptosis Enhances BACE Protein Levels and Beta-secretase Activity in Various Cell Types We examined whether the apoptosis-mediated increase in Aβ generation was associated with changes in the levels and activities of BACE and β-secretase. The first step was to determine whether apoptosis upregulated protein levels of BACE. Western Blot analysis revealed a significant increase of BACE protein levels after 24 hrs of STS treatment in CHO cells overexpressing APP751 and PS1WT (FIG. 3A). In addition, upregulation of BACE occured also in H4 human neuroglioma (FIG. 3B) and in BACE+/+ mouse fibroblasts (FIG. 3C). BACE-/- mouse fibroblasts were used to show the specificity of the antibody used to detect BACE (FIG. 3C). Inhibition of caspase activity by zVAD (100 µM) prevented BACE upregulation in all cell types. As a control for protein loading, the same blot was reprobed with an anti-Cu, Zn-SOD Ab showing that protein levels of Cu, Zn-SOD did not change. These results indicate that caspase activation clearly induced up-regulation of protein levels of BACE in a cell type-independent fashion.

Figure 4:
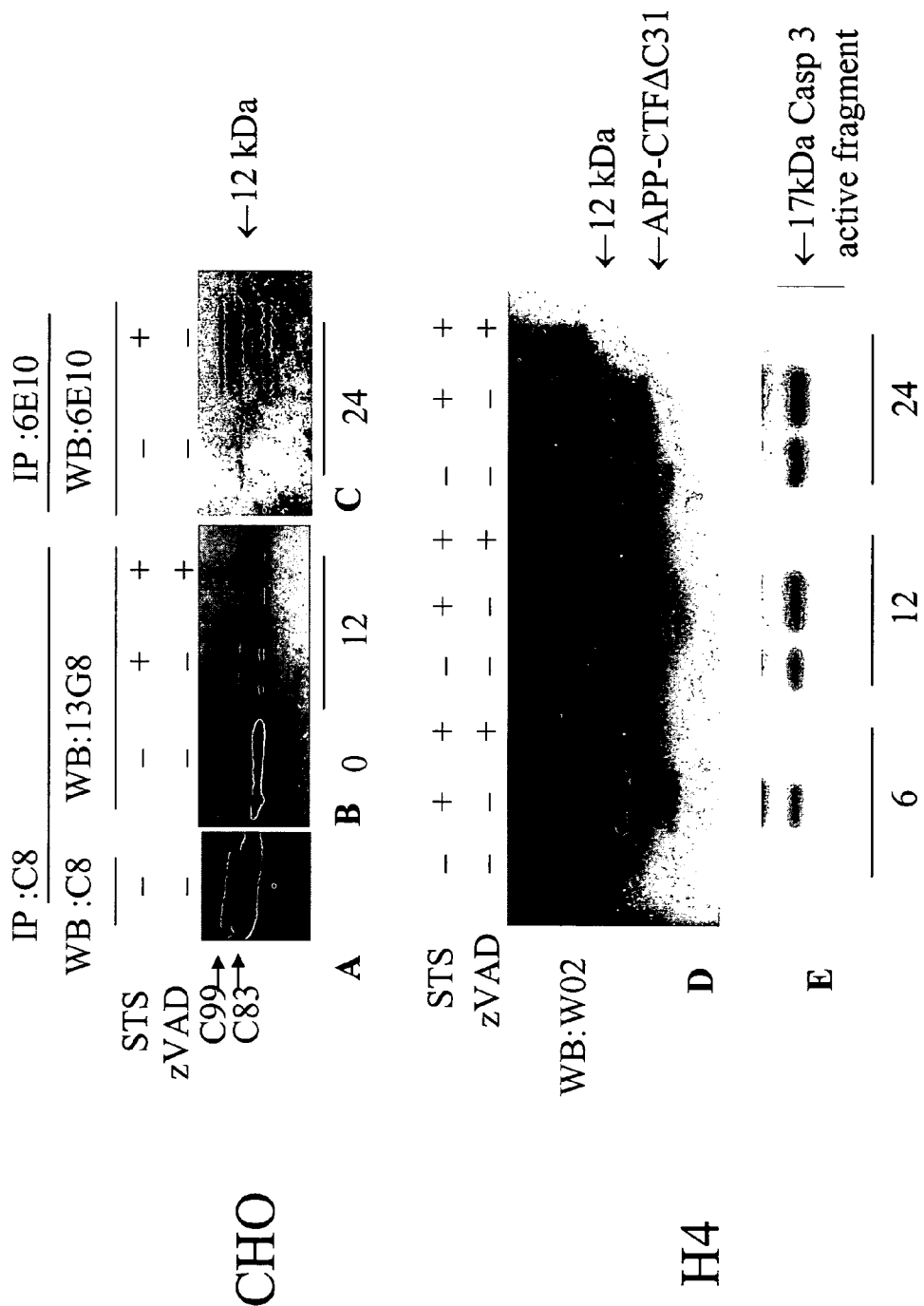
FIG. 4 shows digitized images of immunoprecipitation and Western blot analysis indicating that APP-C99 generated by β-secretase proteolysis of APP was increased in both CHO and H4 cells during apoptosis. Immunoprecipitation (IP) was performed in lysates from CHO cells either with C8, a polyclonal APP C-terminus antibody (FIG. 4B), or 6E10 Ab which recognizes 1-17 amino acids of Aβ region (FIG. 4C). Then, immunocomplexes were detected either with C8 (FIG. 4A), a monoclonal APP C-terminus antibody, 13G8, (FIG. 4B) or 6E10 (FIG. 4C). APP-C83 and three additional bands of ~12, 15 and ~21 kDa were detected in STS treated cells but not in cells treated with both zVAD and STS (FIG. 4B). When IP was performed from an increased amount of protein, both C99 and C83 were isolated in control cells using C8, and C99 did appear to co-migrate with the 12 kDa caspase-derived fragment (FIG. 4A). In addition IP/WB with 6E10 Ab, which specifically recognizes C99, confirmed the same pattern of caspase proteolysis (FIG. 4C) and detected another caspase-derived fragment (indicated by *) of molecular weight lower than C83. The fragments of ~15 and 21 kDa are most likely generated by caspase cleavage, at D544, and at D608. Western blot analysis performed with WO2 Ab, which recognizes 1-17 amino acids of Aβ, revealed APP-C99 in apoptotic H4 cells (FIG. 4D). A fragment of 6.5 kDa which is generated by caspase-mediated cleavage of APP-CTF at D720 and thus, (APP-CTFΔC31) was also detected. In addition, a fragment of ~21 kDa was detected in the STS treated samples, consistent with a caspase-mediated proteolysis at D544 (FIG. 4D). Western blot analysis with an antibody that specifically recognizes the active fragment. The detection of APP-C99 in the untreated cells at time point 24 hrs. was due to caspase activation by serum deprivation (FIG. 4E).

To determine whether the increased protein level of BACE corresponded to an increased β-secretase activity we examined whether apoptosis increased the Aβ-secretase-mediated processing of APP (APP-CTFC99). CHO cells express low levels of BACE and APP-C83, generated by α-secretase is the most abundant species of APP-CTF. Thus, in order to isolate APP-C99 we performed immunoprecipitation/Western Blot (IP/WB) using different anti-APP antibodies. In addition to the normal APP-C83, three additional bands of ~12, 15 and ~21 kDa were detected in the apoptotic cells but not in cells treated with both zVAD and STS (FIG. 4B). When IP was performed from an increased amount of protein, both C99 and C83 were isolated in control cells using an APP C-terminal Ab, C8, and C99 did appeared to co-migrate with the 12 kDa caspase-derived fragment (FIG. 4A). In addition IP/WB with 6E10 Ab, which specifically recognizes C99, confirmed the same pattern of caspase proteolysis (FIG. 4C) and detected another caspase-derived fragment (indicated by *) of molecular weight lower than C83. The latter is likely the product of additional caspase cleavage occurring at a later time point (24 hr) or to post-transcriptional alterations of APP-CTF associated with apoptosis (e.g. dephosphorylation). The molecular size of the fragments of ~15 and 21 kDa was consistent with the presence of a caspase 3 like site, DEVD, at D544, and a novel putative caspase 1-like site, FGAD, at D608. APP-C99 was also detected in apoptotic H4 cells using WO2 Ab, which recognizes 1-17 amino acids of Aβ region. A fragment of 6.5 kDa which was generated by caspase-mediated cleavage of APP-CTF at D720 and thus, lacking the last 31 amino acids (APP-CTFΔC31) was also detected. In addition, a fragment of ~21 kDa was detected in the STS treated samples, consistent with a caspase-mediated proteolysis at D544 (FIG. 4D). The detection of APP-C99 in the untreated cells at time point 24 hrs was due to caspase activation by serum deprivation (FIG. 4E). All the experiments were performed in serum free media and H4 cells seemed to be susceptible to undergo caspase activation by serum deprivation. Our studies of APP processing demonstrate that caspase activation leads to the generation of a 12 kDa fragment, which is most likely C99 in both hamster and human cell lines indicating that caspase activation enhances Aβ-secretase activity.

Example 3

Figure 5:
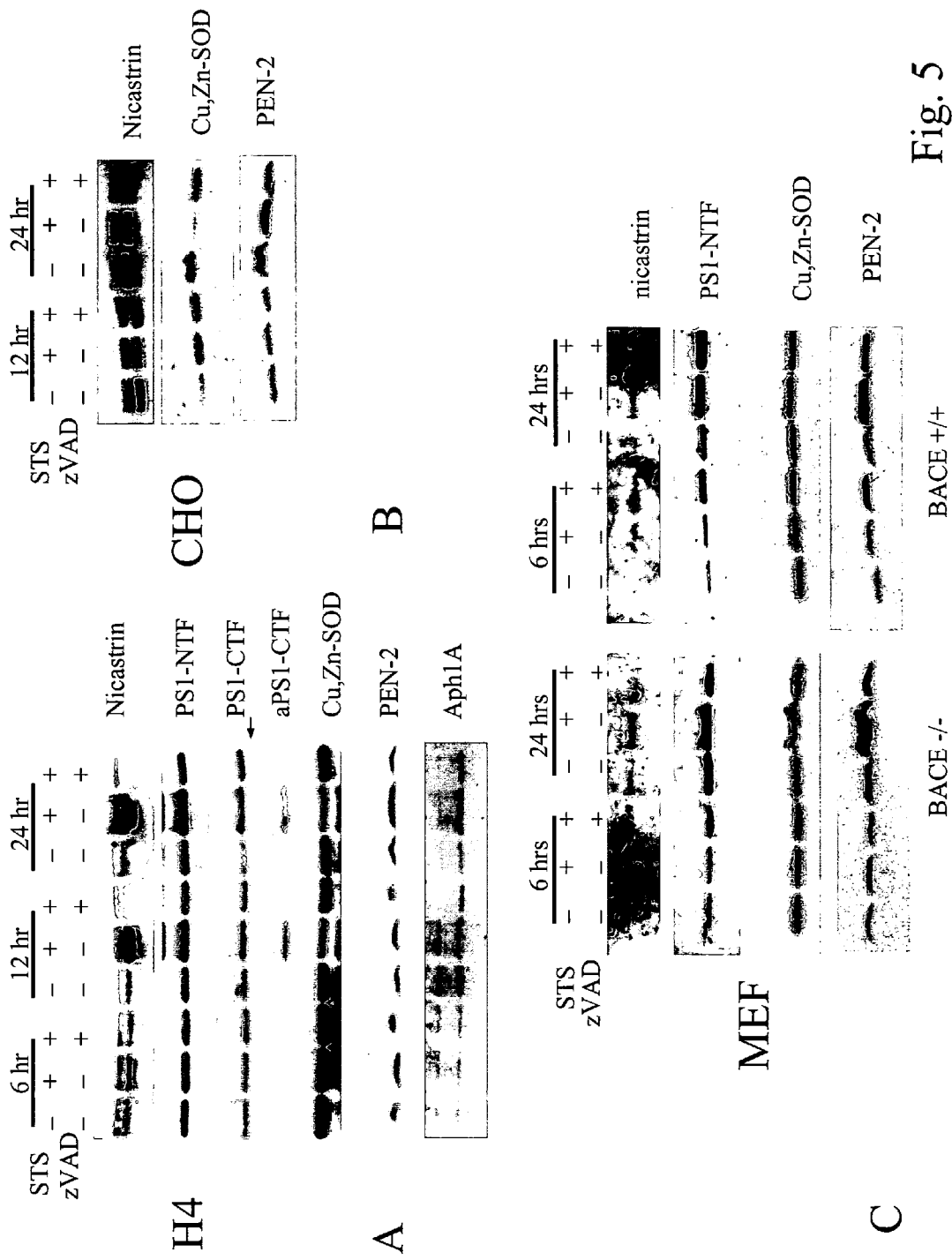
FIG. 5 shows digitized images of Western blots indicating that apoptosis upregulates protein levels of γ-secretase complex proteins in a cell-type and BACE-independent fashion. Protein levels of PS1, nicastrin, Pen2 and Aph1 A (components of the γ-secretase complex) were determined by Western blot (WB) analysis in H4 cells. The immature form of nicastrin appears to be increased earlier (6 hrs) concurrently with caspase-3 activation (FIG. 5A). Furthermore, PS1-NTF, PS1-CTF, Pen2, and Aph1A were also up regulated (FIG. 5A). PS1-CTF undergoes caspase-mediated cleavage as shown by the detection of a caspase-mediated fragment of PS1-CTF (indicated by an arrow and termed aPS1-CTF). Caspase inhibition (zVAD treatment) prevented upregulation of all three proteins. As a control for protein loading, the same blot was reprobed with an anti-Cu, Zn-SOD Ab showing that Cu, Zn-SOD protein levels were not increased. The results confirmed that STS treatment up regulates nicastrin and Pen2 in CHO cells overexpressing APP751 and PS1WT (FIG. 5B) and in mouse fibroblasts (FIG. 5C). Nicastrin, Pen2 and PS1-NTF were upregulated in both BACE−/− and +/+fibroblasts, indicating that the upregulation of three essential components of the γ-secretase complex is BACE-independent.

Apoptosis Enhances γ-Secretase Complex Protein Levels in a Cell Type and BACE Independent Fashion Given that in H4 cells the APP-C99 detected in STS treated samples did not increase over the time and in CHO cells the increase in C99 is detected only upon IP suggesting a rapid degradation, we examined whether there was a parallel increase in γ-secretase activity along with β-secretase activity. We also examined whether the known components of the γ-secretase complex were upregulated during apoptosis. Protein levels of PS1, nicastrin, Pen2 and Aph1A (components of the γ-secretase complex) were determined by Western blot (WB) analysis in H4 cells. Nicastrin protein levels were significantly increased. The immature form of nicastrin appeared to be increased earlier (6 hrs) concurrently with caspase-3 activation (FIG. 5A). Furthermore, PS1-NTF, PS1-CTF, Pen2 and Aph1A were also up regulated (FIG. 5A). STS treatment also led to the generation of a caspase-mediated fragment of PS1-CTF (indicated by an arrow as a PS1-CTF). Caspase inhibition (zVAD treatment) prevented upregulation of all three proteins. As a control for protein loading, the same blot was reprobed with an anti-Cu, Zn-SOD Ab showing that Cu, Zn-SOD protein levels were not increased. These results indicate that caspase activation clearly induces up regulation of protein levels of PS1, nicastrin, Pen2, and Aph1.

We also confirmed that STS treatment up-regulated nicastrin and Pen2 in CHO cells overexpressing APP751 and PS1WT (FIG. 5B) and in mouse fibroblasts (5C). Nicastrin, Pen2 and PS1-NTF were upregulated in both BACE−/− and +/+ fibroblasts, indicating that the upregulation of three essential components of the γ-secretase complex is independent from the presence of BACE.

Example 4

Apoptosis Stabilizes BACE and γ-Secretase Complex Proteins

Figure 6A:
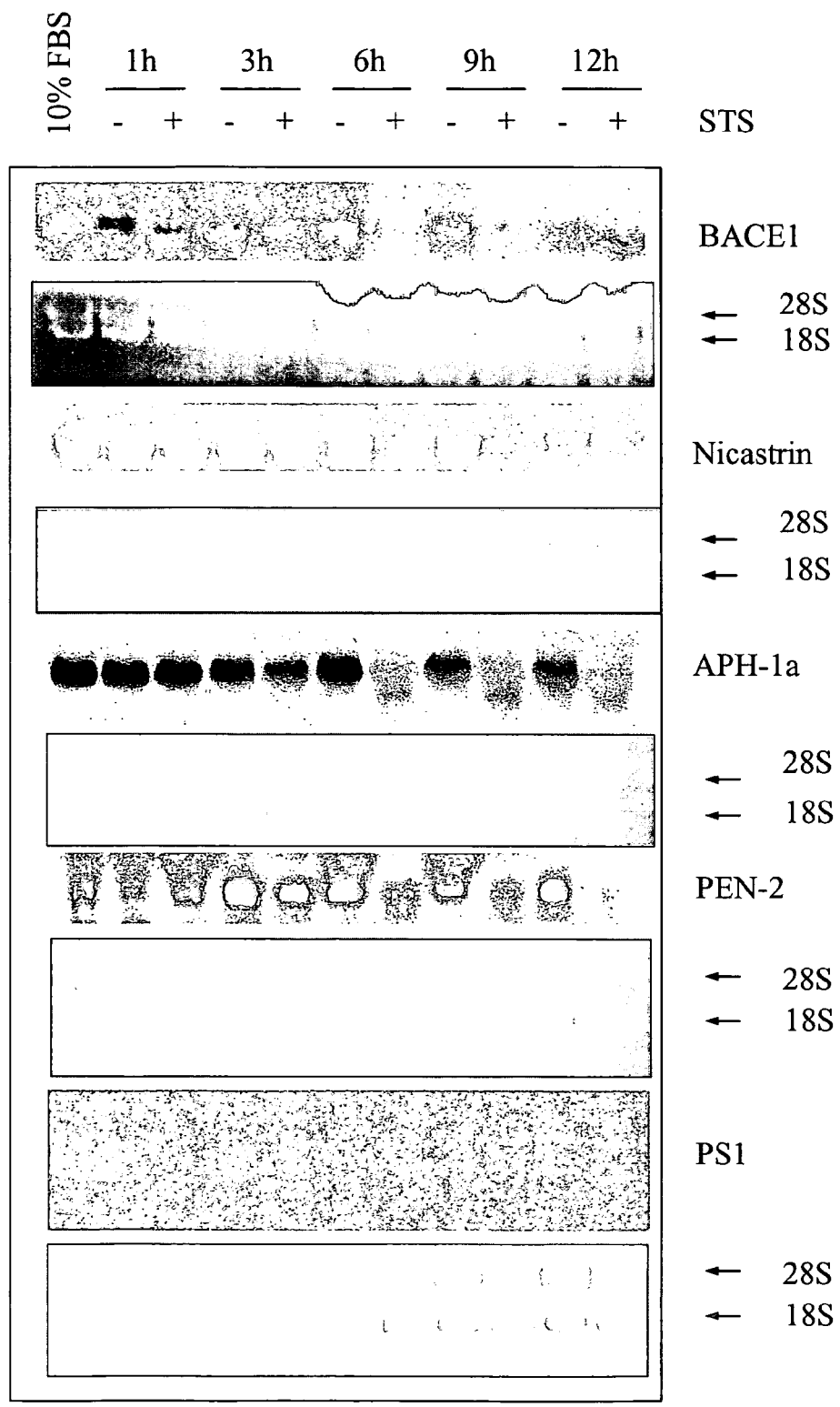
FIG. 6A. Northern Blot analysis reveled that while BACE, nicastrin and Pen2 and Aph-1 mRNA were downregulated, PS1mRNA was upregulated during apoptosis. Ethidium staining of the gel confirmed equal RNA loading.

In order to determine whether STS induced BACE, PS1, nicastrin, Pen2, and Aph1accumulation by altering its synthesis mRNA levels were measured. These experiments indicated that although BACE, nicastrin and Pen2 and Aph-1 mRNA were down-regulated, PS1mRNA was upregulated. Ethidium staining of the gel confirmed equal RNA loading (FIG. 6A).

Figure 6B:
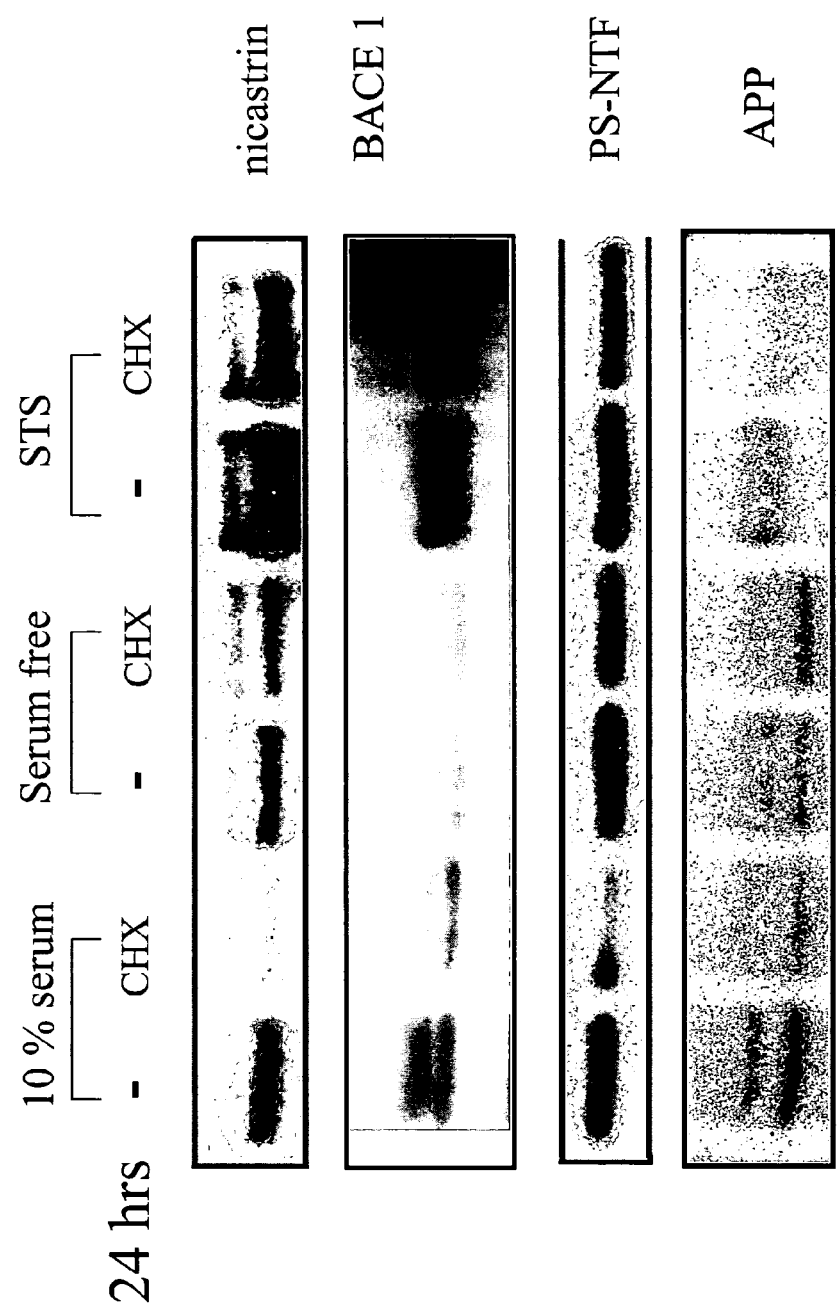
FIG. 6B. To determine whether the accumulation of BACE, PS1nicastrin and Pen2 was independent from protein synthesis H4-APP751 cells were treated with cycloheximide or with cycloheximide plus STS. As expected protein levels of presenilin 1, nicastrin, BACE and APP all diminished over time in normal growth condition (10% serum) and in serum free (SF). However, cycloheximide treated did not affect proteins levels of presenilin 1, BACE, and nicastrin during STS treatment. Instead, APP exhibited a normal rate of turnover during apoptosis.

We next investigated how BACE, nicastrin and Pen2 protein levels were increased during apoptosis while their mRNA levels were clearly decreased. First, we tested whether the BACE, nicastrin and Pen2 protein levels were increased due to decreased turnover of these proteins during apoptosis. For this purpose, we performed degradation time courses by blocking protein synthesis with cycloheximide and then observing protein levels during apoptosis. In H4-APP751 cells treated with cycloheximide alone, protein levels of presenilin 1, nicastrin, BACE, and APP all diminished over time, as expected. However, when cycloheximide was added simultaneously with induction of apoptosis (using staurosporine), presenilin 1, BACE, and nicastrin did not exhibit any visible evidence of turnover by Western blot analysis, and they persisted at constant levels. In contrast, APP exhibited a normal rate of turnover under these conditions (FIG. 6B). These data indicated that during apoptosis, presenilin 1, nicastrin, Pen2 and BACE proteins are stabilized and protected from degradation (while APP is not) accounting for their increased accumulation. These data indicated that PS1is upregulated at the transcriptional level and suggest that PS1might be involved in BACE, nicastrin and Pen2 stabilization.

Example 5

Figure 7:
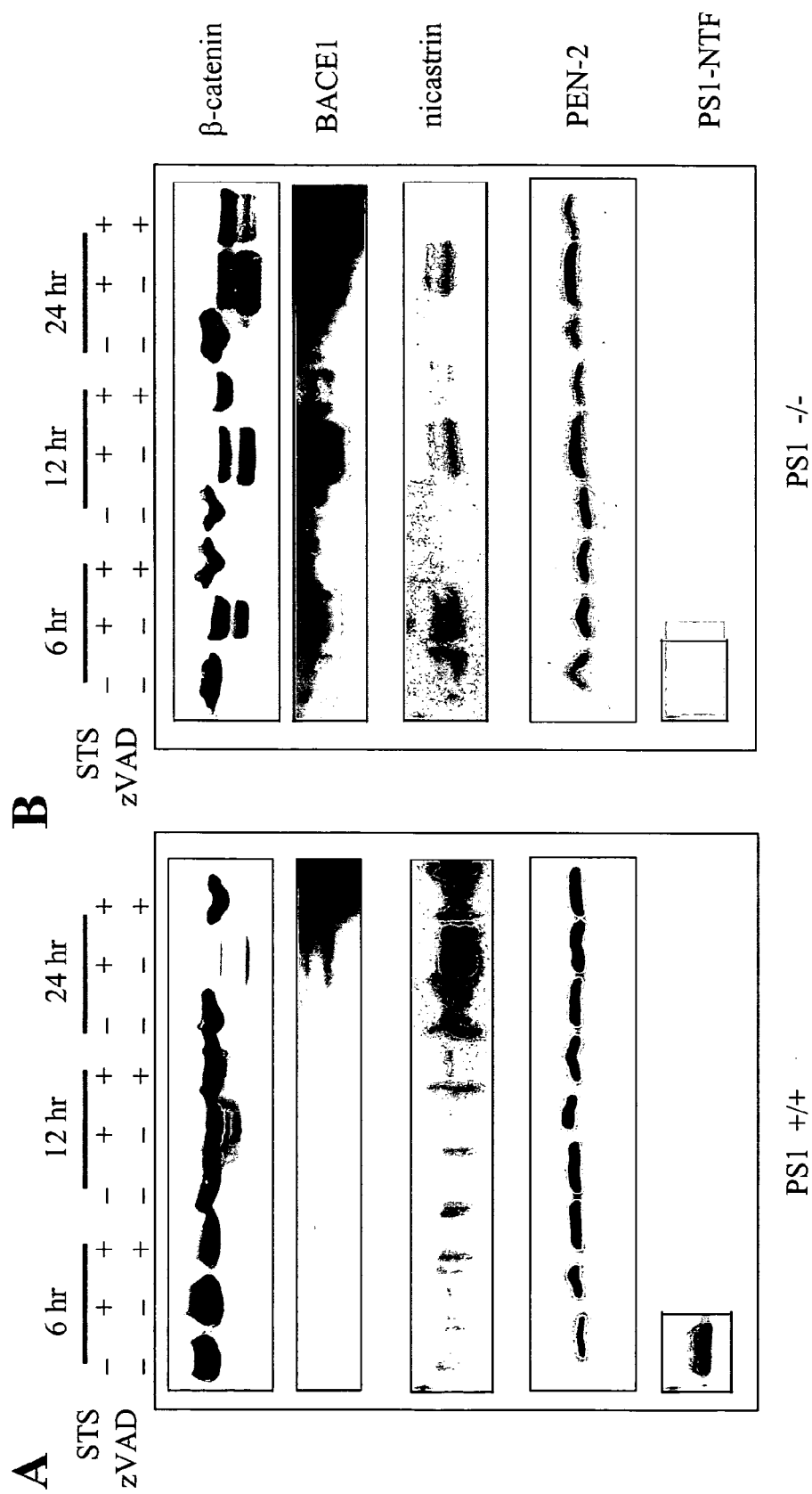
FIG. 7 shows digitized images of Western blot results indicating that BACE, Nicastrin and Pen2 are stabilized in a PS1-independent fashion during apoptosis. Apoptosis was induced by STS treatment in PS1−/−, +/+ mouse fibroblasts (FIGS. 7A and B). BACE, nicastrin and Pen2 were up regulated in PS1+/+ and PS1−/− mouse fibroblasts. Nicastrin and Pen2 levels were decreased in PS1−/− cells compared to control cells. Western blot analysis of β-catenin showed that PS1−/− cells undergoes caspase activation at earlier time points than PS1+/+cells. Western blot analysis with an anti-PS1 N-terminus antibody identified PS1−/− versus PS1+/+ cells.

BACE, Nicastrin and Pen2 are Stabilized in a PS1-independent Fashion During Apoptosis We examined whether stabilization of BACE, nicastrin and Pen2 is PS1-dependent. Apoptosis was induced by STS treatment in PS1−/−, +/+ mouse fibroblasts [(J. Shen et al., Cell 89, 629-39 (1997)]. As expected, BACE, nicastrin and Pen2 were up-regulated in PS1+/+ fibroblasts. BACE, nicastrin and Pen2 were also up regulated in PS1−/− cells. As previously reported [D. Edbauer, et al., Proc Natl Acad Sci USA 99, 8666-71 (2002)], the absence of PS1 impaired nicastrin maturation in control cells, but did not prevent nicastrin up regulation and maturation during apoptosis. As previously reported, Pen2 levels were decreased in PS1−/− cells control cells but induction of apoptosis was still able to upregulate Pen2 in absence of PS1. Interestingly, caspase activation occured at earlier time points (6 hrs) in PS1−/− cells as shown by β-catenin caspase-mediated cleavage suggesting the PS1might have anti-apoptotic function (FIG. 7).

Example 6

Figure 8:
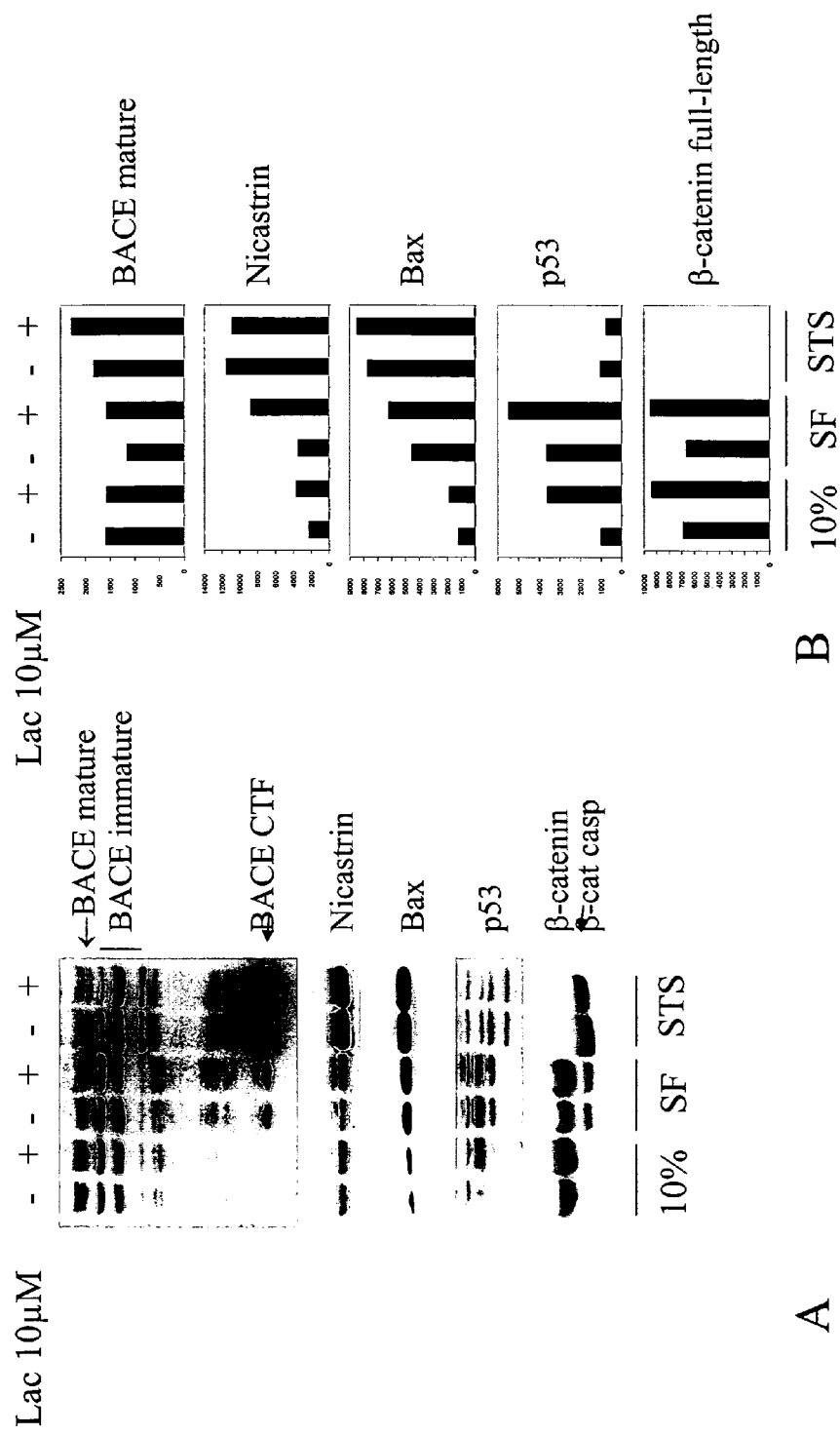
FIG. 8 shows digitized images of Western blots and bar graphs indicating that the proteasome degrades nicastrin but not BACE.
Figure 8C:
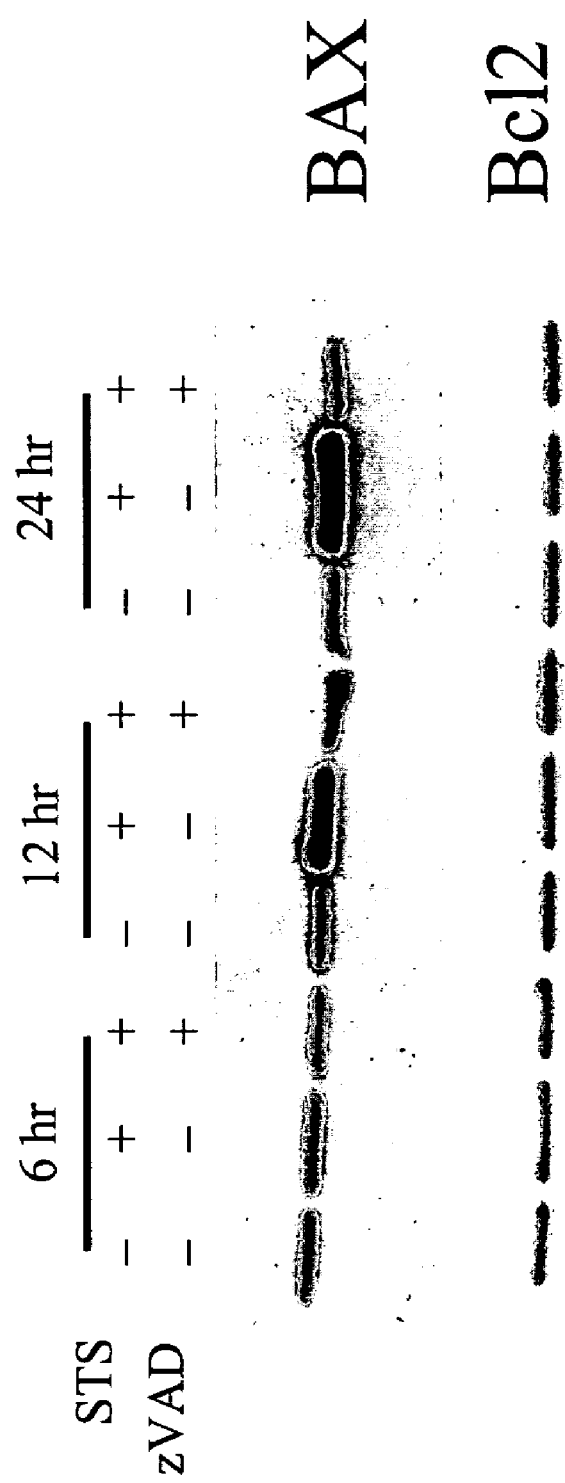
(FIG. 8A) Western blot analysis showed that the inhibition of the proteasome by Lactacystin (10 µM for 24 hrs) increased protein levels of nicastrin but not BACE in normal growth conditions (medium containing 10% Serum). Levels of proteins known to be degraded by the proteasome, Bax, p53, and β-catenin were also increased. Serum deprivation (SF) induced caspase activation as shown by β-catenin caspase-mediated cleavage, and potentiated the effect of proteasome inhibition. Staurosporine (STS) treatment did not induced p53 stabilization in H4 cells and induced a complete caspase-mediated cleavage of α-catenin. Furthermore, STS treatment increased protein levels of nicastrin, Bax and BACE (mature and immature forms) (FIG. 8A). Densitometric analysis was performed with NIH image and reported in bar graphs (FIG. 8B). In addition, apoptosis stabilizes Bax but not Bcl2 during apoptosis in H4 cells (FIG. 8C) ruling out the possibility of a general impairment of proteasome activity.

Stabilization of BACE and γ-secretase Complex Proteins is not due to a Lack of Proteasome Activity Associated with Apoptosis To determine whether the proteasome is the proteolytic pathway responsible for BACE and nicastrin degradation we tested the effect of lactacystin, a highly selective inhibitor of the proteasome. Lactacystin treatment did not affect BACE full length and BACE-CTF levels thus these results excluded a role of the proteasome in BACE degradation. Instead the proteasome inhibition increased protein levels of nicastrin as well as Bax and p53, which are known to be stabilized during apoptosis and to be degraded by the proteasome (FIGS. 8A-B). Thus, stabilization of BACE and nicastrin appeared to be mediated by different mechanisms. In addition, apoptosis stabilizes Bax but not Bcl2 during apoptosis in H4 cells (FIG. 8C). Given that both Bax and Bcl2 were degraded by the proteasome, if apoptosis impaired the proteasome activity an accumulation of both proteins would be expected. Instead the mechanisms of protein stabilization associated to apoptosis seem to be specific and thus, they are likely regulated.

Discussion

Collectively these data demonstrated that increased production of Aβ during apoptosis or following caspase activation is due to increased protein levels of the protease and protease complex proteins that cleave APP to produce Aβ including the protease, BACE, and the γ-secretase complex components, presenilin 1, nicastrin, Pen2, and Aph1A. The Northern and Western blot time course data suggested the following course of events to explain increased Aβ production following the induction of caspase activation and/or apoptosis: 1) presenilin 1 transcription is increased and presenilin 1 protein levels increase; 2) nicastrin levels increase most likely due to stabilization by the increased amounts of presenilin 1; and 3) BACE levels are increased most likely due to stabilization by increased levels of nicastrin. This results in increased β- and γ-secretase activity and would then explain the observed increase in production of Aβ during apoptosis. Upregulation of BACE, nicastrin, Pen2, and Aph1A in PS1−/− cells may be the result of upregulation of PS2. If PS1−/−PS2−/− cells still show stabilization of these proteins, additional presenilin-independent factors may be implicated.

Example 7

Methods and Materials

Chemicals and Antibodies

Staurosporine, cycloheximide, L-685,458 and GM6001 were purchased from Calbiochem (La Jolla, Calif.). zVAD was purchased from Enzyme System Products. The anti-caspase 3 active fragment and anti-Myc antibodies were purchased from Cell Signaling Technology, Inc. (Beverly, Mass. 01915). The anti-E-cadherin C36 monoclonal antibody was purchased from Transduction Laboratories (Lexington, Ky.). The anti-BACE C-terminal antibody and anti-nicastrin antibody were purchased from Affinity Bioreagents (ABR, Golden, Colo.). The polyclonal antibody, A8717, raised against the C-terminus of APP and the anti-β-tubulin antibody were purchased from Sigma (St. Louis, Mo.). The monoclonal antibody, WO2, raised against 1-17 amino acids of Aβ region was a gift of Dr. Beyreuther (University of Heidelberg, Heidelberg, Germany). The anti-TACE antibody was purchased from Santa Cruz Biotechnology, Inc. (Santa Cruz, Calif.). The anti-Cu, Zn-SOD antibody was a gift of Dr. Naoyuki Taniguchi (Osaka University Medical School, Osaka, Japan). The polyclonal antibodies, Ab14 (gift of Dr. Sam Gandy, Thomas Jefferson University, Philadelphia, Pa.), αPS1loop, and αPS2loop (gift of Drs. Sam Sisodia and Gopal Thinakaran (University of Chicago, Chicago, Ill.)) specifically recognize epitopes at the N-terminus and within the hydrophilic loop domain of PS1 and PS2, respectively. The polyclonal antibody, PNT2, was generated against the N-terminal 26 amino acids of Pen-2 (gift of Dr. Thinakaran). The anti-Aph1a antibody, H2D2, was a gift of Dr. Gang Yu (University of Texas Southwestern Medical Center, Dallas, Tex.).

Cell Culture, Western Blot Analysis and Induction of Apoptosis

Chinese Hamster Ovary (CHO) cells expressing APP751 and BACE (CAB), CHO cells expressing full-length APP and wild-type PS1 (CHO-APP751/PS1) or expressing C99 and wild-type PS1 (CHO-CC99/PS1), H4 human neuroglioma cells expressing APP751 (H4-APP751), mouse embryonic fibroblast (MEF), embryonic stem (ES) cells, and human epithelial A431 cells were grown as described previously (Marambaud, P. et al., *Embo J* 21, 1948-56 (2002); Cai, H. et al., *Nat Neurosci* 4, 233-4 (2001); Sato, N. et al., *Nat Cell Biol* 2, 863-70 (2000); Puglielli, L., Ellis, B. C., Saunders, A. J. & Kovacs, D. M., *J Biol Chem* 278, 19777-83 (2003); Wolfe, M. S. et al., *Nature* 398, 513-7 (1999)). For the induction of apoptosis, we used staurosporine or etoposide (Calbiochem (EMD Biosciences, San Diego, Calif.)). For Aβ measurements, cells were seeded at the density of $0.5 \times 10^6$ cells per well in 6 well plates. After 48 hours, cells were treated with either STS (1 μM) for 6 hours. In order to inhibit caspase activation a sister plate of cells was pre-treated with zVAD (100 1M, Enzyme Systems Products) for 1 hour before STS treatment. For time-course experiments, cells were seeded at the density of $2 \times 10^6$ cells per 100 mm dish and treated with STS (1 μM) or etoposide (100 μg/mL). At different time points (0, 3, 6, 9, 12 and 24 hours), the cells were scraped, centrifuged and then lysed in buffer containing 1% NP40. Western blot analysis was performed as previously described (Tesco, G., Koh, Y. H. & Tanzi, R. E., *J Biol Chem* 278, 46074-80 (2003)). Densitometry analysis was performed on a Macintosh computer using the public domain NIH Image program (developed at the U.S. National Institutes of Health and available on the Internet at http://rsb.info.nih.gov/nih-image/).

Aβ ELISA

Secreted $A\beta_{1-total}$ was measured in the conditioned media of untreated cells or of cells treated with STS or STS plus zVAD using a sensitive ELISA (Wolfe, M. S. et al., *Nature* 398, 513-7 (1999). At least three different experiments were carried out and each experiment was performed at least in triplicate.

Cycloheximide Degradation Time-course

H4-APP751 cells were treated with CHX (40 μg/ml) only or STS (1 μM)+CHX during a 30 h time-course. Lysates from each time point were immunoblotted with the specific antibodies, anti-BACE, Ab14, anti-nicastrin, PNT2, H2D2, anti-TACE, and the anti-APP antibody, A8717.

Metabolic Labeling and Pulse-chase Experiments

H4-APP751 cells were preincubated in methionine/cysteine-free (starve) medium for 30 min after which they were incubated in starve medium supplemented with 1 mCi of [$^{35}$S]methionine/cysteine per well for 60 min (pulse). Then, cells were incubated in the presence of excess amounts of cold methionine/cysteine for indicated time (chase). The cells were then washed, lysed in radioimmunoprecipitation assay (RIPA) buffer (1% sodium deoxycholate, 0.1% SDS, 1% Triton X-100, 5 mM EDTA, 50 mM Tris, pH 8, 150 mM NaCl), and immunoprecipitated with the specific antibodies. Samples were separated by SDS-PAGE using 4-12% gels, fixed, dried, and exposed to film or a phosphorimaging screen (Bio-Rad, Hercules, Calif.). Images were analyzed using a Personal Molecular Imager FX and quantified using Quantity One software (Bio-Rad). For BACE pulse-chase experiments, the anti-BACE antibodies were unable to immunoprecipitate endogenous BACE. Thus, H4-APP751 cells were transfected with 10 μg of pcDNA-BACE-myc cDNA using Superfect according to the manufacturer's protocol. At 24 hours following transfection, cells were harvested and pulled together to avoid difference in transfection efficiency and plated again. After 24 hours, cells were metabolically labeled as described above. For PS1pulse-chase experiments, H4 cells stably transfected with wild-type PS1 (H4-PS1) were used.

Results

Figure 9:
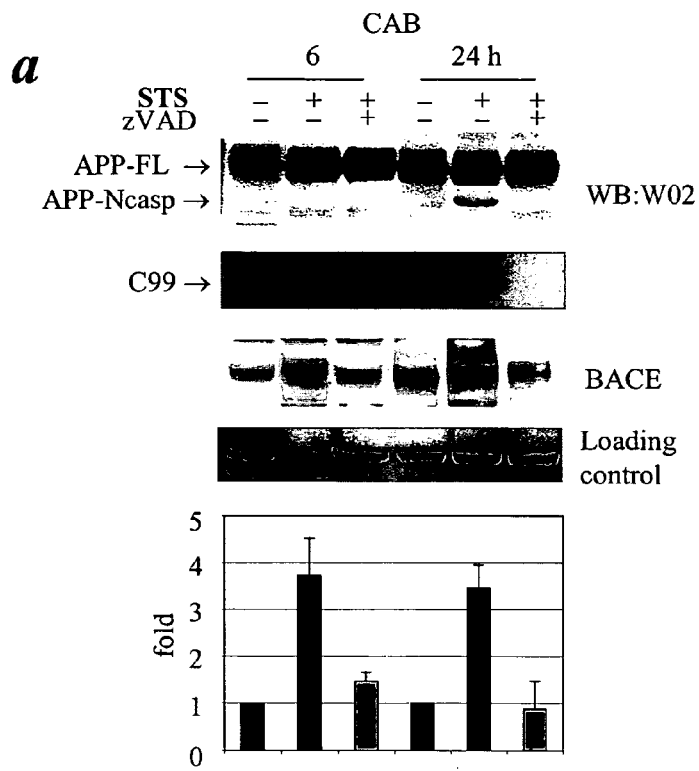
FIG. 9 provides digitized images and graphs showing that caspase activation enhances β-secretase-mediated processing of APP and protein levels of BACE.
Figure 9:
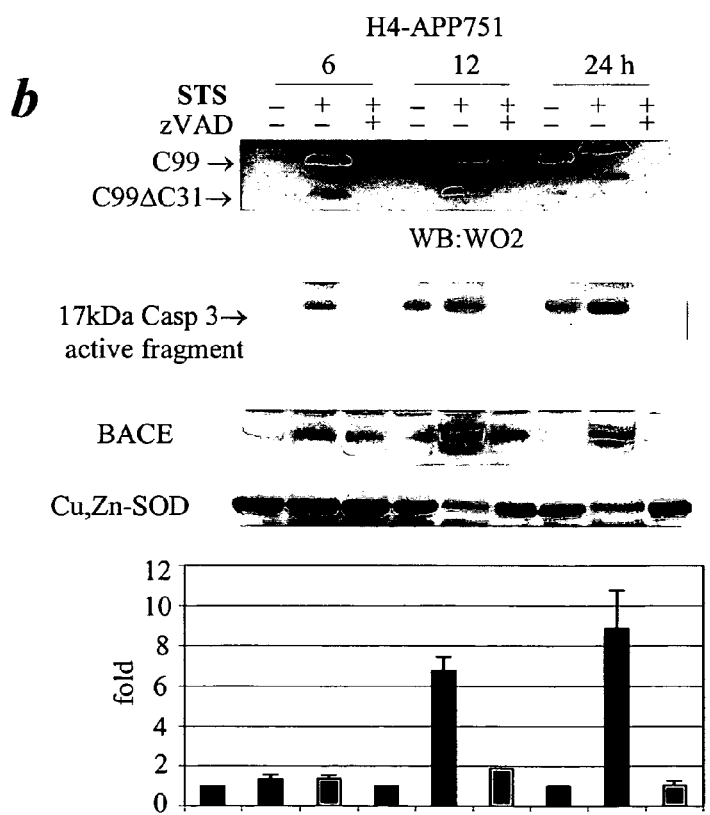

It has been previously shown that overexpression of BACE enhances β-secretase cleavage of APP leading to the accumulation of intracellular C99 (Vassar, R. et al., *Science* 286, 735-41 (1999)). We first asked whether apoptosis/caspase activation leads to accumulation of C99 owing to increased β-secretase activity. Apoptosis induced by staurosporine (STS) resulted in increased levels of C99 in CHO cell lines expressing APP751 and BACE (CAB). APP caspase-mediated cleavage (APP-Ncasp) was also detected, as shown above. Furthermore, BACE protein levels were increased ~4-fold after 6 hours or 24 hours of STS treatment, in CAB cells (FIG. 9a). These data indicate that β-secretase activity increases during apoptosis. These findings were also confirmed in H4 human neuroglioma cells expressing APP751 (H4-APP751), in SH-SY5Y and N2a cells (FIG. 10c), and in naive CHO cells (data not shown) expressing only endogenous BACE. A 6.5 kDa fragment corresponding to caspase cleavage at D720 (C99ΔC31) was also detected in apoptotic H4-APP751 as previously described (Tesco et al., 2003). A small increase of C99 in the untreated cells at time point 12 and 24 hours was most likely due to low level caspase activation owing to the fact that the control cells were grown in serum-free media (FIG. 9b). Inhibition of caspase activity by zVAD prevented BACE accumulation in both CAB and H4-APP751 cells (FIGS. 9a-b).

Figure 10:
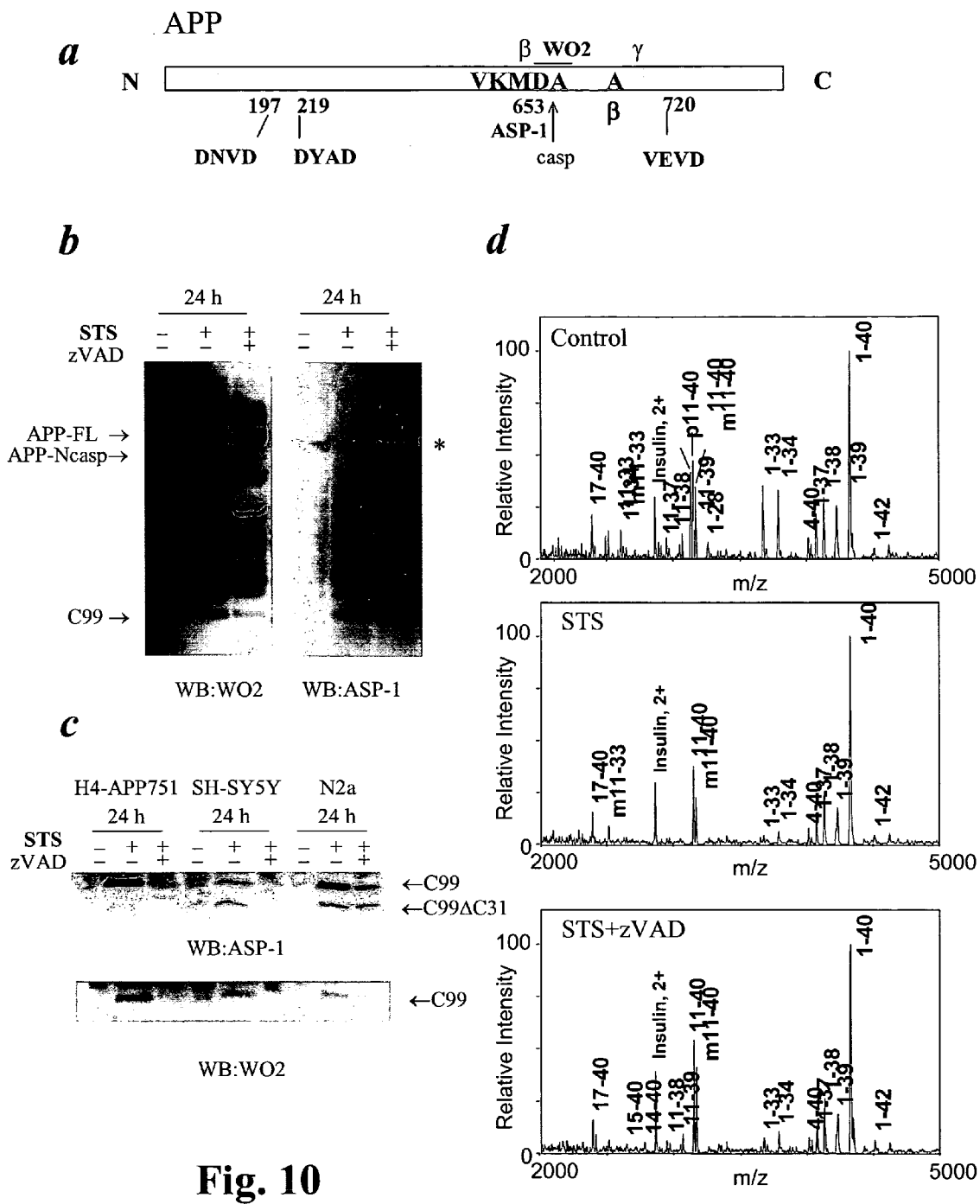
FIG. 10 provides schematic drawings, digitized images and graphs indicating that caspase-mediated cleavage at D653 is not involved in increased Aβ generation during apoptosis.

A putative caspase 6-like site (VKMD, SEQ ID NO:1) has been previously identified at D653 in the β-secretase region of APP (Gervais, F. G. et al., *Cell* 97, 395-406 (1999); LeBlanc, A., Liu, H., Goodyer, C., Bergeron, C. & Hammond, J., *J Biol Chem* 274, 23426-36 (1999)). However, we were able to rule out a role for this site in enhancing the generation of APP-CTF and Aβ during apoptosis based on a number of criteria, including mass spectral analysis (FIG. 10).

Figure 11:
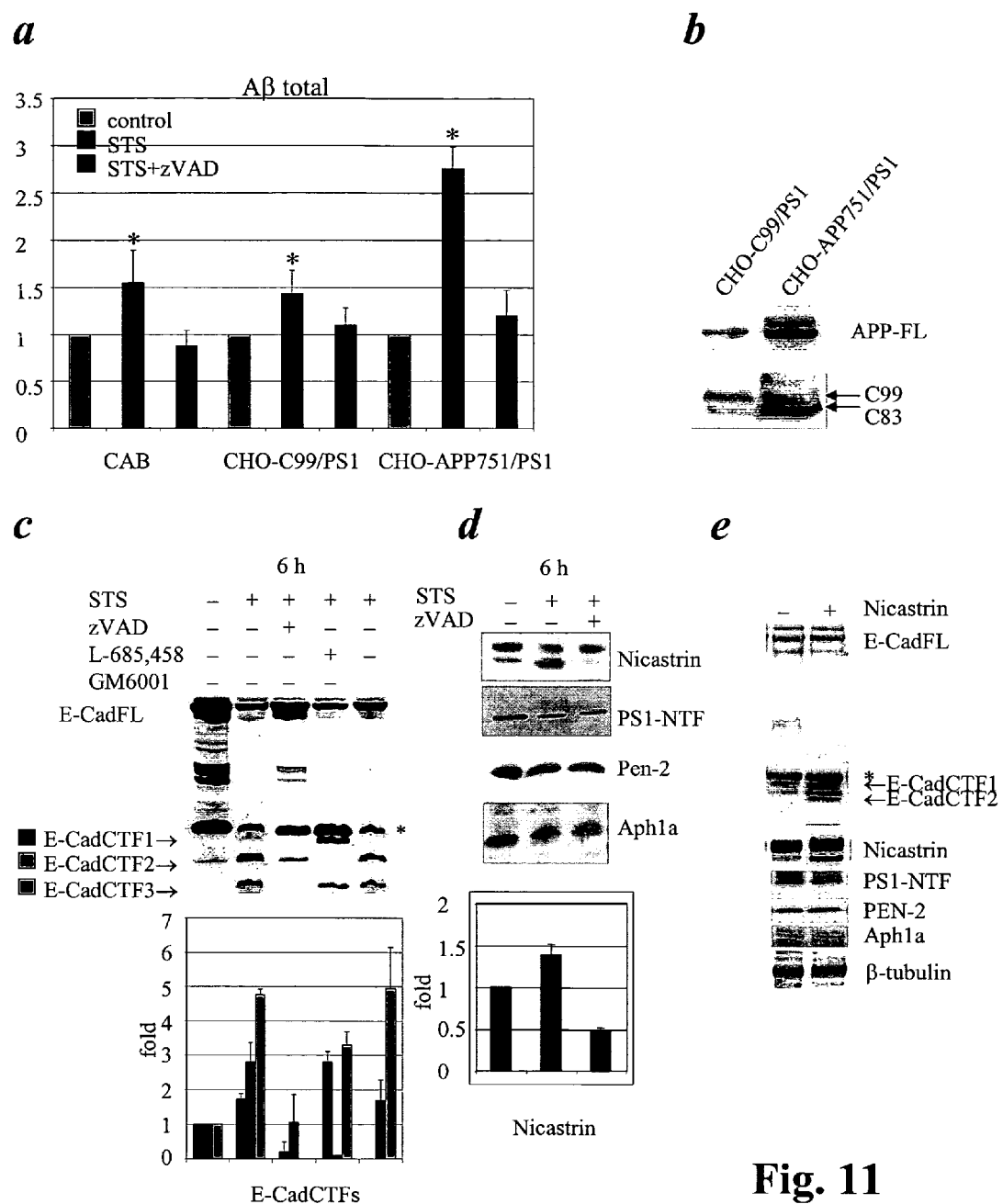
FIG. 11 provides digitized images and graphs showing that apoptosis enhances γ-secretase activity and levels of γ-secretase complex proteins.

Although the increased levels of C99, resulting from increased Aβ-secretase activity, were sufficient to significantly increase $A\beta_{1-total}$ production during apoptosis (FIG. 11a CAB), we next asked whether γ-secretase activity further potentiates Aβ production following caspase activation. To answer this question, we first induced apoptosis in CHO cells expressing both C99 and wild-type PS1 (CHO-CC99/PS1) by STS treatment. $A\beta_{1-total}$ was increased ~1.5 fold in STS-treated CHO-CC99/PS1 cells compared to untreated cells owing to increased γ-secretase activity (FIG. 11a). In comparison, $A\beta_{1-total}$ increased ~2.5 fold in STS-treated CHO cells expressing both full-length APP and wild-type PS1 (CHO-APP751/PS1) (FIG. 11a) suggesting that β- and γsecretase activities most likely exert additive effects on Aβ generation during apoptosis. The expression of full length APP and C99 is shown in FIG. 11b.

To confirm that apoptosis/caspase activation increases γ-secretase activity, we next examined the proteolysis of E-cadherin, another γ-secretase substrate (Marambaud, P. et al., *Embo J* 21, 1948-56 (2002)) during apoptosis. We confirmed that caspase activation enhanced the production of E-Cad/CTF1 (Steinhusen, U. et al., *J Biol Chem* 276, 4972-80 (2001)), E-Cad/CTF2 (Marambaud, P. et al., 2002) (~2- and 3-fold increase by densitometry analysis, respectively), and generated E-Cad/CTF3 (Marambaud, P. et al., 2002) (FIG. 11c). The generation of E-Cad/CTF1, E-Cad/CTF2, and E-Cad/CTF3 is inhibited by treatment with the MMP inhibitor, GM6001, the γ-secretase inhibitor, L-685, 458, and the caspase inhibitor, zVAD, respectively. These data indicate that E-Cad/CTF1, E-Cad/CTF2, and E-Cad/CTF3 are generated by a matrix metalloprotease (MMP), γ-secretase, and caspases, respectively. The inhibition of caspase activity prevented the increase in E-Cad/CTF1 and E-Cad/CTF2, and E-Cad/CTF3 generation, indicating that caspase activation increases MMP and γ-secretase activity (FIG. 11c). However, as we observed for BACE, caspase activation increased the γ-secretase proteolysis of E-Cad independently of the MMP cleavage. This is evidenced by increased production of E-Cad/CTF2 even when MMP activity was inhibited by GM6001 treatment (FIG. 11c). Moreover, since E-Cad/CTF2, unlike Aβ, is not secreted, the increased generation of E-Cad/CTF2 indicates that caspase activation increases γ-secretase activity independently of any potential effects on secretion of its proteolytic products.

We next examined whether levels of the γ-secretase complex proteins were increased following caspase activation. We found that immature nicastrin levels were increased by ~1.5-fold after 6 hours of STS treatment (FIG. 11d) in the A431 cells, concurrently with the observation of increased γ-secretase activity (FIG. 11c). However, protein levels of PS1, Pen-2 and Aph1 a were unchanged (FIG. 11d). Mature and immature nicastrin, PS1-NTF, and Pen-2 were increased at later time points (48h) (data not shown). Furthermore, the overexpression of nicastrin in the A431 cells was able to increase E-Cad/CTF2 generation, while protein levels of the other γ-secretase complex components were unchanged (FIG. 11e). These data are in general agreement with a previous report showing that the individual expression of nicastrin increases γ-secretase activity (Murphy, M. P. et al., *Faseb J* 17, 1138-40 (2003)).

Figure 12:
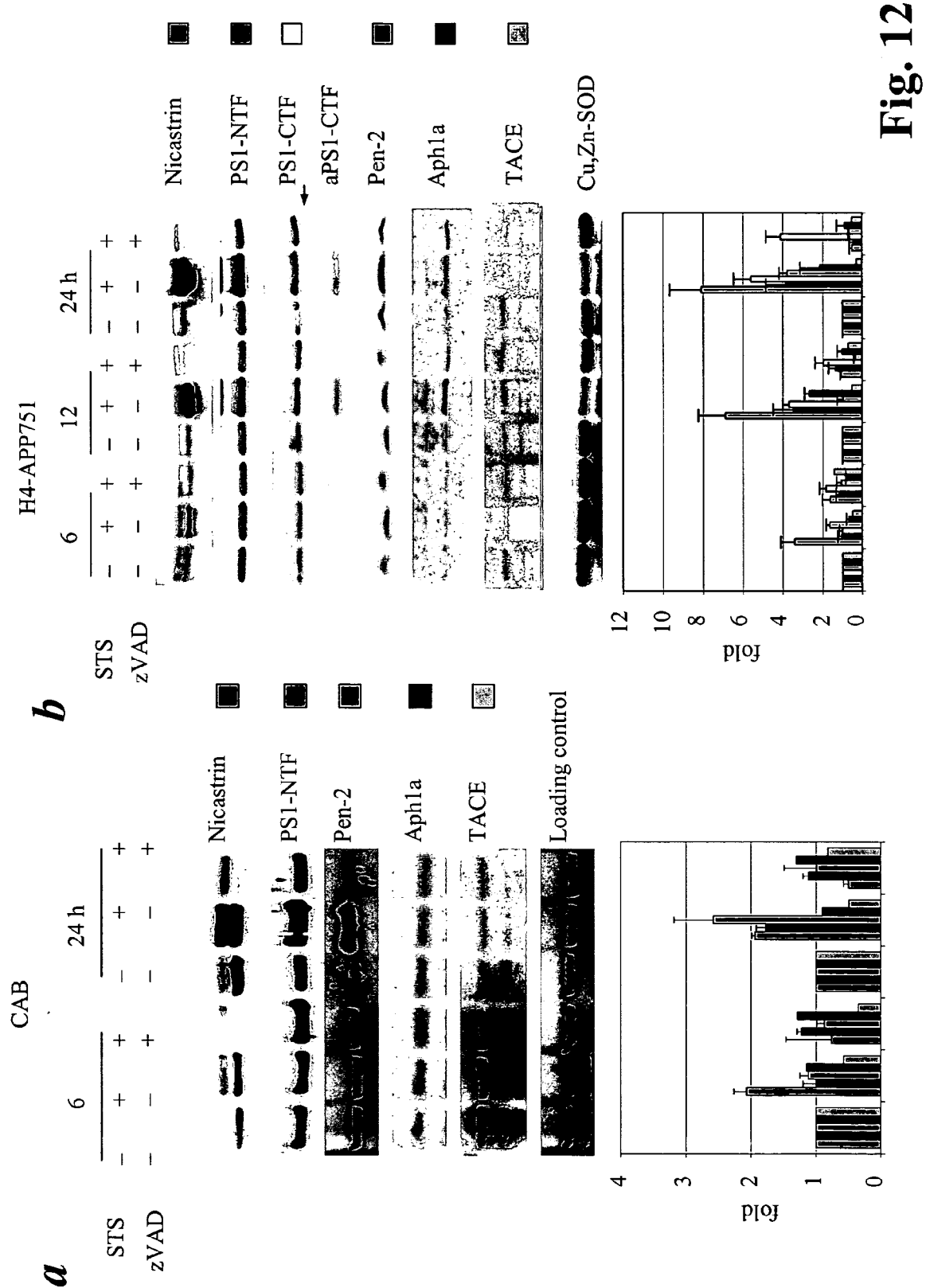
FIG. 12 provides digitized images and graphs showing that apoptosis increases levels of γ-secretase complex proteins. CAB cells and H4-APP751 cells were treated with STS (FIG. 12a and FIG. 12b, respectively). Equivalent amounts of protein from each sample were immunoblotted with anti-nicastrin, Ab14, αPS1 loop, PNT2, H2D2, and anti-TACE antibodies. A non-specific band was used as a loading control for the CAB cells, while Cu, Zn-SOD was used for the H4-APP751 cells. STS treatment also led to the generation of a caspase-derived fragment of PS1-CTF indicated as "a" (alternative) PS1-CTF (Kim, T. W., Pettingell, W. H., Jung, Y. K., Kovacs, D. M. & Tanzi, R. E., *Science* 277, 373-6 (1997)) (FIG. 12b). Densitometry analysis was performed using NIH image software. Each bar represents the mean and SEM of at least three experiments.

Six hours after STS treatment, we observed an increase in endogenous nicastrin protein levels that concurred with increased Aβ production in CAB cells. In contrast, endogenous levels of PS1 and Pen-2 were increased only at later time point (24h) (FIG. 12a). These findings were also confirmed in H4-APP751 cells (FIG. 12b). Aph1a protein levels were increased in H4-APP751 cells 12 hours after STS treatment, but not in CAB cells suggesting that the extent of upregulation of γ-secretase complex components during apoptosis may vary in a cell-dependent manner (FIG. 12a-b). Immature nicastrin levels were decreased in the cells treated with STS plus zVAD when compared to the untreated control cells, most likely owing to inhibition of a low level caspase activity induced by serum deprivation in the control cells. As a negative control, protein levels of the candidate α-secretase, TACE, were not increased in both CAB and H4-APP751 cells (FIGS. 12a-b).

Figure 13:
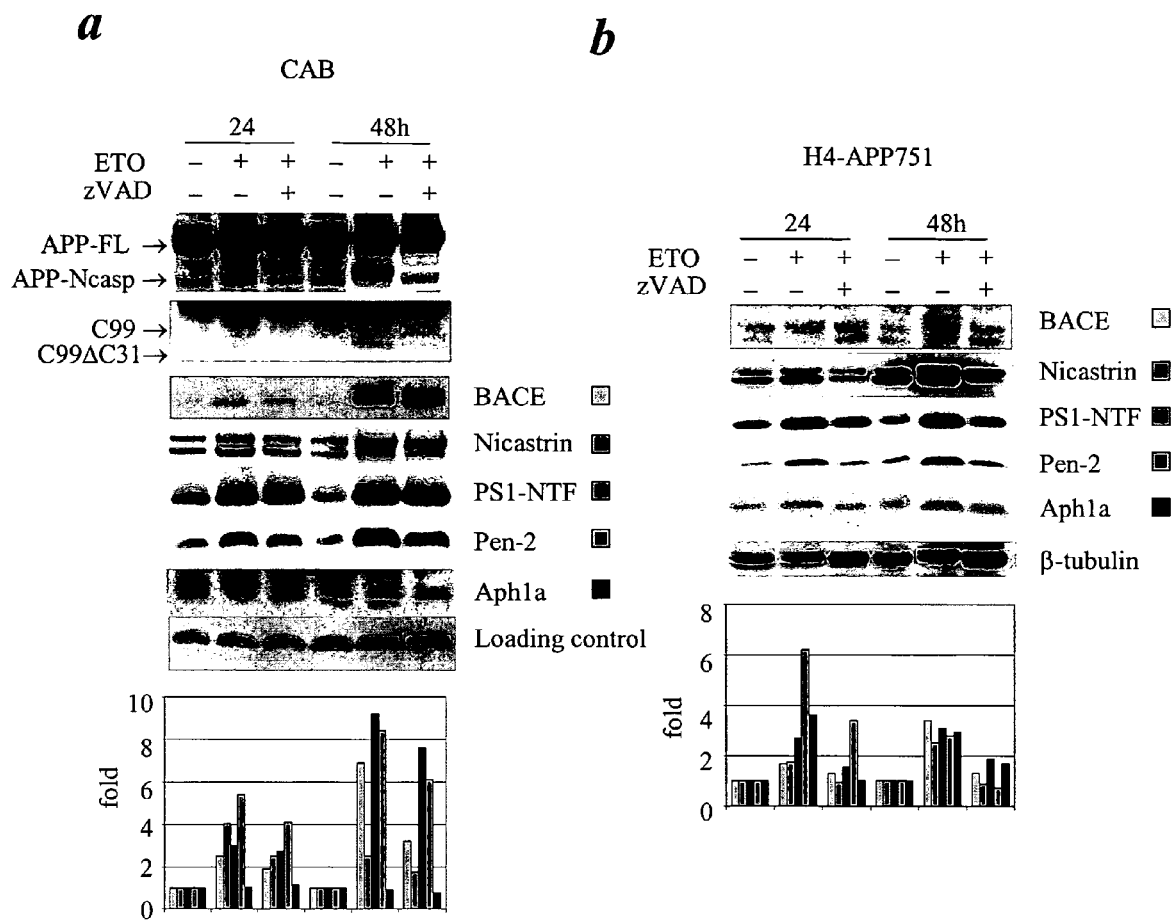
FIG. 13 provides digitized images and graphs indicating that etoposide-induced apoptosis increases levels of C99, BACE, and γ-secretase complex proteins.

Collectively, these findings indicate that caspase activation increases both γ-secretase activity and the levels of γ-secretase complex proteins in a wide variety of cell lines. However, the increase of immature nicastrin precedes the increase of the other γ-secretase complex proteins, concurrently with increased γ-secretase activity. The complex glycosylation events that distinguish mature from immature nicastrin are not necessary for γ-secretase activity or for binding to PS1 (Herreman, A. et al., *J Cell Sci* 116, 1127-36 (2003)). Thus, the observed increase in immature nicastrin protein levels would appear to be sufficient to increase γ-secretase activity, and likely represents the first event in the potentiation of γ-secretase activity at the endogenous level, following caspase activation. All these findings were also observed when apoptosis was induced by etoposide treatment (FIG. 13).

Figure 14:
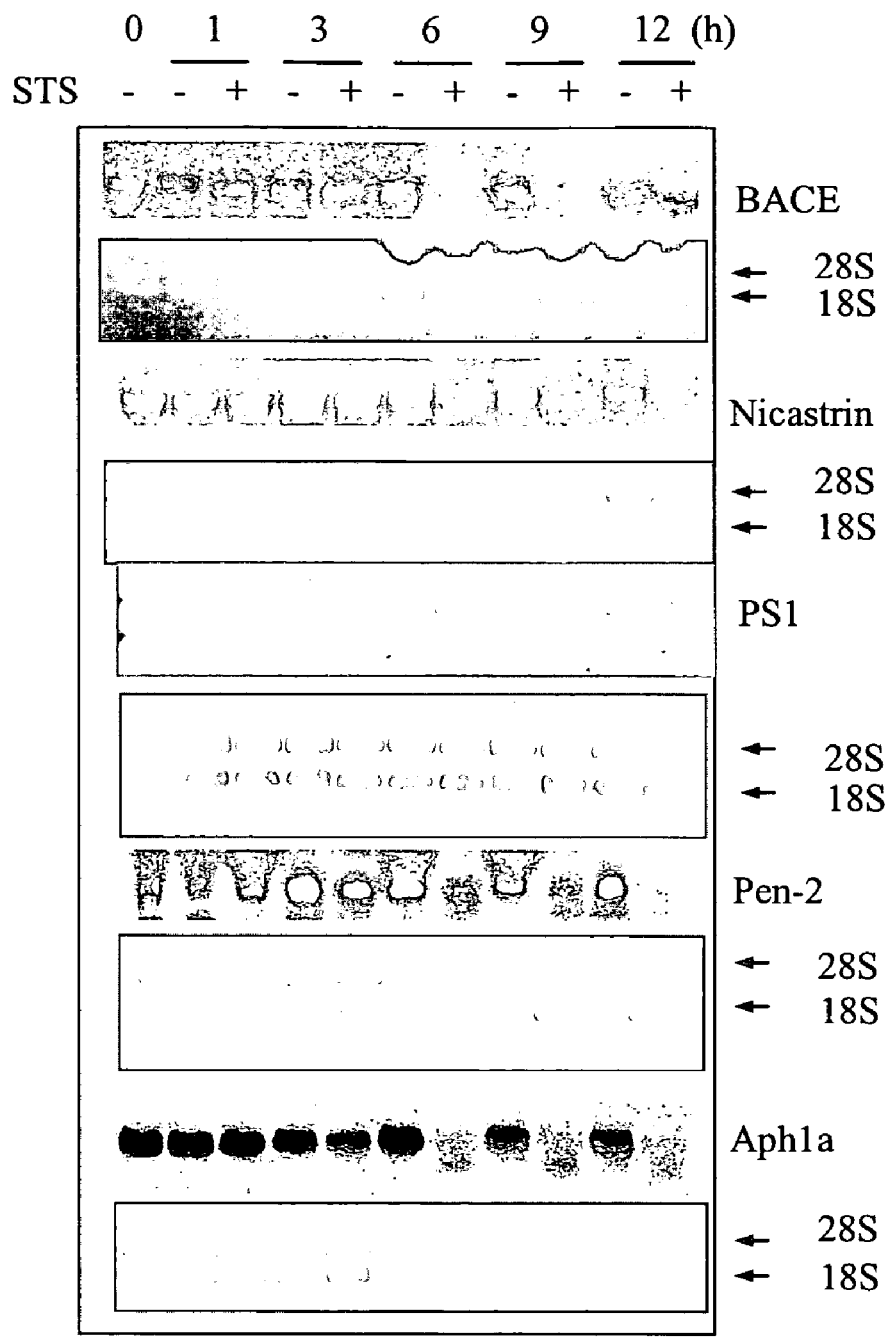
FIG. 14 provides digitized images showing that transcription of BACE and γ-secretase complex components is decreased during apoptosis. Northern Blot analysis: H4-APP751 cells were treated with STS in serum free media. Total RNA was extracted using TRIZOL (Invitrogen). 20 µg of the resulting RNA were analyzed by Northern blot analysis performed as previously described (Koh, Y. H. et al., *Faseb J* 15, 1472-4 (2001)). Human cDNA of BACE, PS1, nicastrin, Pen-2, Aph1a was labeled with [α-$^{32}$P]dCTP (PerkinElmer) using random hexanucleotide primers (Prime-a-gene labeling system; Promega). Ethidium staining of the gel (lower panel) confirmed equal RNA loading.
Figure 15:
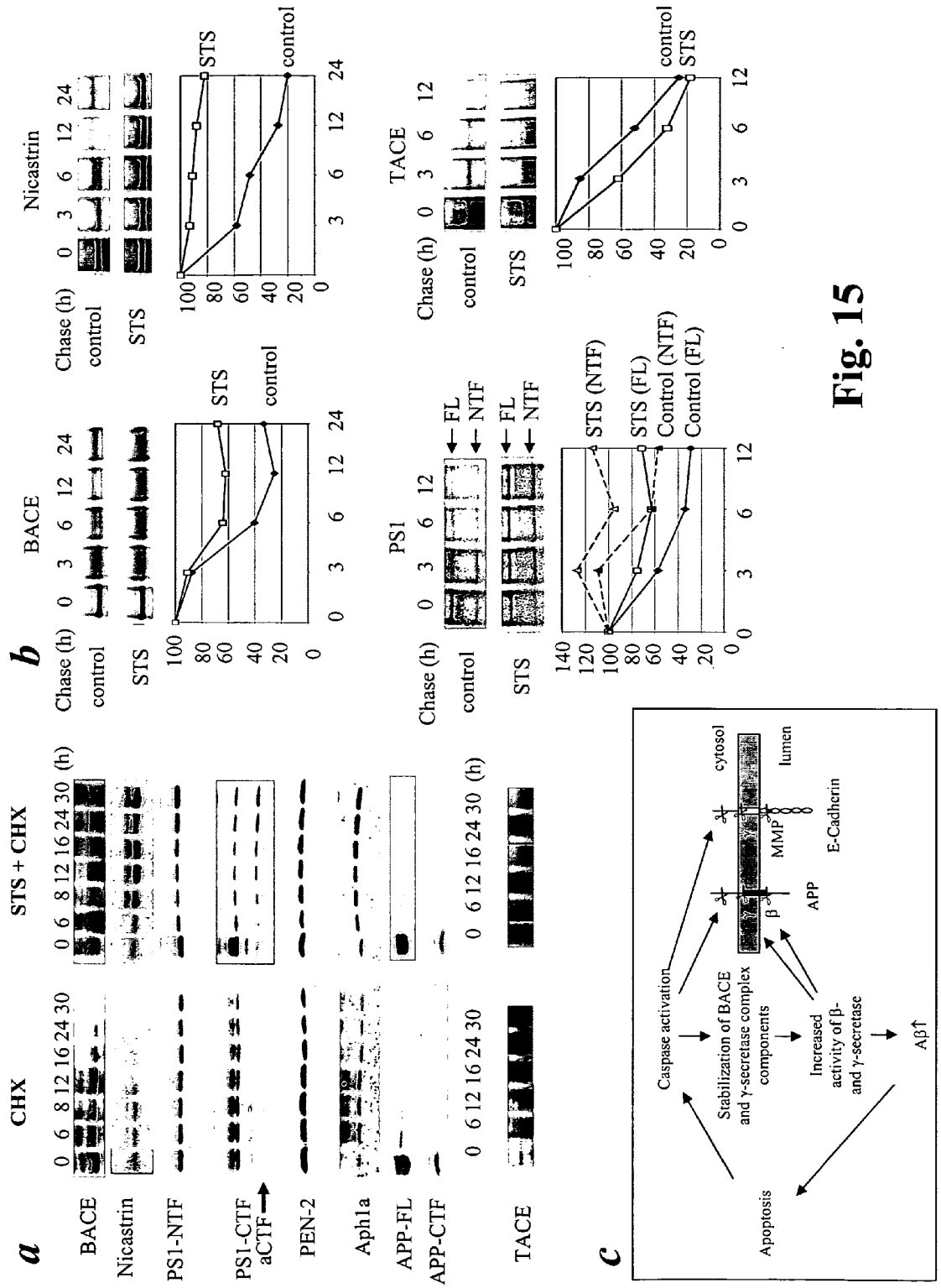
FIG. 15 provides digitized images, graphs and a schematic drawing indicating that caspase activation stabilizes BACE and γ-secretase complex proteins in H4 human neuroglioma cells.

We next asked whether apoptosis increases protein levels of BACE, PS1, nicastrin, Pen-2 and Aph1a via increased synthesis. Interestingly, and in contrast to certain results reported above in Example 4, we found that BACE, PS1, nicastrin, Pen-2 and Aph1a mRNA levels were not increased but instead most of the mRNA for these proteins was virtually undetectable after only 6 hours of STS treatment (FIG. 14) in the H4-APP751 cells. We next asked whether BACE, PS1, nicastrin, Pen-2 and Aph1a protein levels are increased during apoptosis due to decreased degradation. We found that the approximate half-lives of BACE, PS1, nicastrin, Pen-2 and Aph1a ranged from 6 to 18 hours under normal condition in cycloheximide (CHX) time course experiments. However, following caspase activation, the levels of all these proteins did not significantly decrease even after 30 hours into the time-course. In contrast, TACE, full-length APP, and APP-CTFs were not stabilized during apoptosis (FIG. 15a). Given that the components of the β-amyloidogenic secretases are stabilized during apoptosis while many other proteins are degraded (e.g. TACE, APP), the apparent increase of protein levels at the latest time points of the CHX+STS time course was most likely due to a relative increase of stabilized protein when normalized for the equal amounts of total protein.

Pulse-chase analysis revealed an increased half-life of mature and immature BACE (>24 hours vs. ~6 hours in normal conditions) and immature nicastrin (>24 hours vs. 12 hours in normal conditions) during apoptosis (FIG. 15b).

The newly synthesized immature nicastrin undergoes stabilization but not maturation during apoptosis. However, both Western blot analysis and CHX time-course experiments indicated that mature nicastrin, already present in the cell when apoptosis is induced, is also stabilized. Thus, collectively, these data further support a central role for nicastrin stabilization in potentiating γ-secretase activity during apoptosis.

Figure 16:
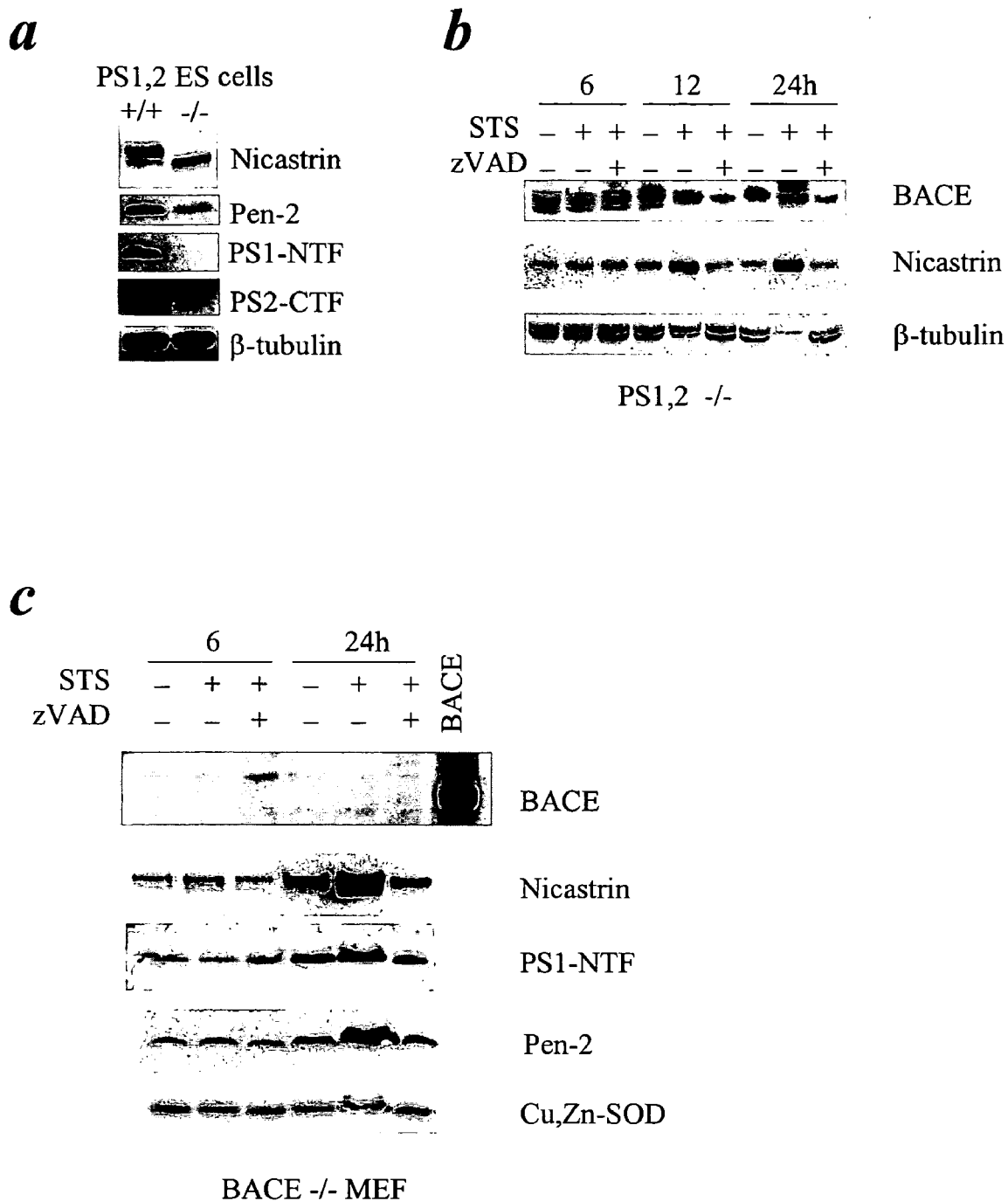
FIG. 16 provides digitized images showing that stabilizing effects of caspase activation on the β-amyloidogenic secretases occur independently of BACE and PS1/2.

Pulse-chase analysis also revealed increased half-lives for full-length PS1 (PS1-FL) and PS1—NTF, while the half-life of the negative control, TACE, was not altered during apoptosis (FIG. 15b). These data indicate that during apoptosis BACE, presenilin 1, nicastrin, Pen-2, and Aph1a proteins are likely protected from degradation accounting for their increased accumulation and enhanced β-amyloidogenic secretase activities. Finally, the stabilization of BACE and nicastrin following caspase activation occurred independently of PS, as evidenced in PS1/PS2−/− ES cells. Likewise, nicastrin, PS1—NTF, and Pen-2 protein were stabilized following caspase activation in BACE−/−MEF (FIG. 16).

We have shown that caspase activation increases the activity of both β- and γ-secretase by stabilizing BACE and the γ-secretase complex proteins. For γ-secretase, stabilization of immature nicastrin represented the first event. This is the first demonstration of increased activity of these disease-related proteases during apoptosis suggesting a novel mechanism for enhanced A, generation following caspase activation. These findings also suggest a potential role for the β amyloidogenic secretases in apoptosis aiding caspases in the proteolysis of transmembrane proteins during apoptosis. In the case of APP, this also leads to increases in Aβ generation. Since Aβ has also been shown to induce apoptosis (Yuan, J. & Yankner, B. A., *Nature* 407, 802-9 (2000)) the result is a vicious cycle of caspase activation and Aβ production ultimately leading to cell death (FIG. 15c).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A method for identifying compounds that modulate caspase activation-induced stabilization of a secretase pathway associated protein comprising contacting cells with a candidate modulator of secretase pathway associated protein stabilization before or after inducing the cells to undergo caspase activation, and measuring the stability of the secretase pathway associated protein, wherein a difference in the stability of the protein relative to the stability of the protein in untreated cells is an indication that the candidate modulator is a compound that modulates the caspase activation-induced stability of the secretase pathway associated protein, wherein the secretase pathway associated protein is selected from the group consisting of: a presenilin, nicastrin/ Aph2, BACE, Aph1a, and Pen-2 protein.

2. The method of claim 1, wherein the secretase pathway associated protein is BACE.

3. The method of claim 1, wherein the cells are neuronal cells.

4. The method of claim 1, wherein the caspase activation induces apoptosis.

5. The method of claim 1, wherein the presenilin is presenilin 1.

6. The method of claim 1, wherein the cells are contacted with the candidate modulator before caspase activation induction.

7. The method of claim 1, wherein the cells are contacted with the candidate modulator after caspase activation induction.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Val Lys Met Asp
1

<210> SEQ ID NO 2
<211> LENGTH: 4
<212> TYPE: PRT
<213> ORGANISM: Homo sapiens

<400> SEQUENCE: 2

Asp Asn Val Asp
1

<210> SEQ ID NO 3
<211> LENGTH: 4
<212> TYPE: PRT
<213> ORGANISM: Homo sapiens

<400> SEQUENCE: 3

Asp Tyr Ala Asp
1

<210> SEQ ID NO 4
<211> LENGTH: 4
<212> TYPE: PRT
<213> ORGANISM: Homo sapiens

<400> SEQUENCE: 4

Val Glu Val Asp
1
```

```
<210> SEQ ID NO 5
<211> LENGTH: 5
<212> TYPE: PRT
<213> ORGANISM: Homo sapiens

<400> SEQUENCE: 5

Val Lys Met Asp Ala
1               5
```